US005986081A

United States Patent [19]

Ganetzky et al.

[11] Patent Number: 5,986,081

[45] Date of Patent: Nov. 16, 1999

[54] POLYNUCLEOTIDES ENCODING HERG-3

[75] Inventors: Barry S. Ganetzky; Steven A. Titus, both of Madison, Wis.

[73] Assignee: Wisconsin Alumni Research Foundation, Madison, Wis.

[21] Appl. No.: 08/956,242

[22] Filed: Oct. 22, 1997

[51] Int. Cl.$^6$ .................................................... C12N 15/12

[52] U.S. Cl. .................... 536/23.5; 435/69.1; 435/252.3; 435/254.11; 435/320.1; 435/325

[58] Field of Search .......................... 536/23.5; 435/69.1, 435/320.1, 325, 252.3, 254.11

[56] References Cited

FOREIGN PATENT DOCUMENTS

WO 96/28537 9/1996 WIPO .

OTHER PUBLICATIONS

Curran et al. "A Molecular Basis for Cardiac Arrhythmia: Herg Mutations Cause Long QT Syndrome", *Cell*, 80: 795–803 (1995).

Hoffman et al., "Overexcited or Inactive: Ion Channels in Muscle Disease", *Cell*, 80: 681–686 (1995).

Miller, Christopher, "The Inconstancy of the Human Heart", *Nature*, 379: 767–768 (1996).

Sanguinetti et al., "Spectrum of HERG $K^+$–channel Dysfunction in an Inherited Cardiac Arrhythmia", *Proc. Natl. Acad. Sci.*, 93: 2208–2212 (1996).

Sanguinetti et al., "A Mechanistic Link Between an Inherited and an Acquired Cardiac Arrhythmia: HERG Encodes the $I_{kr}$ Potassium Channel", 81: 1–20 (1995).

Smith et al., "The Inward Rectification Mechanism of the HERG Cardiac Potassium Channel", *Nature*, 379: 833–836 (1996).

Titus et al., "The Drosophila erg $K^+$Channel Polypeptide is Encoded by the Seizure Locus", *J. Neuroscience*, 17(3): 875–881 (1997).

Trudeau et al., "HERG, a Human Inward Rectifier in the Voltage–Gated Potassium Channel Family", *Science*, 269: 92–95 (1995).

Wang et al., "Positional Cloning of a Novel Potassium Channel Gene: KVLQT1 Mutations in Cause Cardiac Arrhythmias", *Nature Genetics*, 12:17–23 (1996).

Warmke et al., "A Family of Potassium Channel Genes Related to eag in Drosophila and Mammals", *Proc. Natl. Acad. Sci.*, 97: 3438–3442 (1993).

Welsh et al., "Ion Channels Lose the Rhythm", *Nature*, 376(24): 640–641 (1995).

Editoral, "Third and Long (QT)", *Nature Genetics*, 12(1): 1–2 (1996).

*Primary Examiner*—Sally Teng
*Attorney, Agent, or Firm*—Quarles & Brady LLP

[57] ABSTRACT

Novel genes in the erg subfamily of potassium channel proteins in humans are described. This family of proteins, and the genes encoding the proteins, are implicated in the development of long Q-T syndrome rare, but often fatal, cardiac arrhythmia.

12 Claims, 3 Drawing Sheets

Screen Rat Brain cDNA library with Herg probe
- Pulled out rERG 6.1 positive

- 2KB cDNA spanning pore through 3' end
- Similar to 2 dbEST cDNAs
  - F02206: unavailable for purchase
  - 232319: purchased from IMAGE consortium Screen Human Genomic library with 232319 probe
- Pulled out 11.1 positive clone
- Did PCR on 11.1

Primers
seq 5 from F02206
seq 6 degenerate S5
seq 7 degenerate S1
seq 8 from 2kb PCR

```
HERG-1 MPVRRGHVAPQNTFLDTIIRKFEGQSRKFIIANARVENCAVIYCNDGFCELCGYSRAEVMQRPCTCDFLHGPRTQRRAAAQIAQALLGAE 90
HERG-2 MFPR---------------------------------------------ELVSIKPGVAMGRS-------------HTPPLASDLLFSAL 32
HERG-3 ------------------------------------------------------------------------------------------ 0

HERG-1 ERKVEIAFYRKDGSCFLCLVDVVPVKNEDGAVIMFILNFEVVMEKDMVGSPAHDTNHRGPPTSWLAPGRAKTFRLKLPALLALTARESSV 180
HERG-2 PLEASVPL----GTCLL----------------------------------------RRPPP---------------------------- 50
HERG-3 ------------------------------------------------------------------------------------------ 0

HERG-1 RSGGAGGAGAPGAVVVDVDLTPAAPSSESLALDEVTAMDNHVAGLGPAEERRALVGPGSPPRSAPGQLPSPRAHSLNPDASGSSCSLART 270
HERG-2 ----------------HLSLIPSAHQSRGH----------------PPSSHYTFPREQ-ESRPVSPALAAECLTSLGEHP---------- 97
HERG-3 ------------------------------------------------------------------------------------------ 0

HERG-1 RSRESCASVRRASSADDIEAMRAGVLPPPPRHASTGAMHPLRSGLLNSTSDSDLVRYRTISKIPQITLNFVDLKGDPFLASPTSDREIIA 360
HERG-2 ------------------------------------------------------------------------------------------ 97
HERG-3 ---------------------------------------------------------------------------------------IIA 3

HERG-1 PKIKERTHNVTEKVTQVLSLGADVLPEYKLQAPRIHRWTILHYSPFKAVWDWLILLLVIYTAVFTPYSAAFLLKETEEGPPATECGYACQ 450
HERG-2 ---------------QVLSLGADVLPEYKLQAPRIHRWTILHYSPFKAVWDWLILLLVIYTAVFTPYSAAFLLSDQDESRRG-ACEYTCS 171
HERG-3 PKVKDRTHNVTEKVTQVLSLGADVLPEYKLQTPRINKFTILHYSPFKAVWDWLILLLVIYTAIFTPYSAAFLLNDREEQKRR-ECGYSCS 92

HERG-1 PLAVVDLIVDIMFIVDILINFRTTYVNANEEVVSHPGRIAVHYFKGWFLIDMVAAIPFDLLIFGSGSEE---LIGLLKTARLLRLVRVAR 537
HERG-2 PLTVVDLIVDIMFVVDIMINFRTTYVNTNDEVVSHPRRIAVHYFKGWFLIDMVAAIPFDLLIFRTGSDETTTLIGLLKTARLLRLVRVAR 261
HERG-3 PLNVVDLIVDIMFIIDILINFRTTYVNQNEEVVSDPAKIAXHYFKGWFLIDMVAAIPFDLLIFGSGSDETTTLIGLLKTARLLRLVRVXR 182

HERG-1 KLDRYSEYGAAVLFLLMCTFALIAHWLACIWYAIGNMEQPHMDSRIGWLHNLGDQIGKPYNSSG-LGGPSIKDKYVTALYFTFSSLTSVG 626
HERG-2 KLDRYSEYGAAVLFLLMCTFALIAHWLACIWYAIGNVERPYLEHKIGWLDSLAVQLGKRYNGSDPASGPSVQDKYVTALYFTFSSLTSVG 351
HERG-3 KLDRYSEYGAAVLMLSMCIFALNAHWLACIWYAIGNVERPYLTDKIGWLDSLGQQIGKRYNDSDSSSGPSIKDKYVTALYFTFSSLTSVG 272
```

Fig. 2A

```
HERG-1 FGNVSPNTNSEKIFSICVMLIGSLMYASIFGNVSAIIQRLYSGTARYHTQMLRVREFIRFHQIPNPLRQRLEEYFQHAWSYTNGIDMNAV 716
HERG-2 FGNVSPNTNSEKVFSICVMLIGSLMYASIFGNVSAIIQRLYSGTARYHMQMLRVKEFIRFHQIPNPLRQRLEEYFQHAWTYTNGIDMNMX 441
HERG-3 FGNVSPNTNSEKIFSICVMLIGSLMYASIFGNVSAIIQRLYSGTARYHMQMLRVKEFIRFHQIPNPLRQRLEEYFQHAWTYTNGIDMNMV 362

HERG-1 LKGFPECLQADICLHLNRSLLQHCKPFRGATKGCLRALAMKFKTTHAPPGDTLVHAGDLLTALYFISRGSIEILRGDVVVAILGKNDIFG 806
HERG-2 XXXXXXXX-------------------------------------------------------------TR------------- 451
HERG-3 LKGFPECLQADICLHLNQTLLQNCKAFRGASKGCLRALAMKFKTTHALQGDTLVHCGDVLTALYFLSRGSIEISKXXLVVAILGKNDIFG 452

HERG-1 EPLNLYARPGKSNGDVRALTYCDLHKIHRDDLLEVLDMYPEFSDHFWSSLEITFNLRDTNMIPG---SPGSTELEGGFSRQRKRKLSFRR 893
HERG-2 ---------GKSSADVRALTYCDLHKIQRADLLEVLDMYPAFAESFWSKLEVTFNLRD---------------------------------- 500
HERG-3 EMVHLYAKPGKSNADVRALTYCDLHKIQREDLLEVLDMYPEFSDHFLTNLELTFNLRHESAKADLLRSQSMNDSEGDNCKLRRRKLSFES 542

HERG-1 RTDKD--IEQPGEVS-ALGPGRAGAGPSSRGRPGGPWGESP-------------SSGPSSPESSEDEGPGRSSSP-------------LRLV 956
HERG-2 ------------------------AAGGLH-----------------S---------SPR-------QAPG----------SQDHQ--GF--- 521
HERG-3 EGEKENSINDSEDSADTIRHYQSSXXPLXRKKADPELSSPELMMNKXLFSGIVDSSPXIGEAEGLXFXXTCPPPGECPXLXXPLAXXSWL 632

HERG-1 PFSSPRPPGEPPGGEPLM---EDC------------------EKSSDTCNPLSGAFSGVSNIFSFWGDSRGRQYQELPRCPAPTPSLLNIPL 1027
HERG-2 -FLSD----------N-----SQ------MQPLP 533
HERG-3 SXLGXKNS-LERLEXEFLCPSXNCLGFLXXXVSTSGRMHIDKRSHSCKDITDMRS---------WERENAHPQPEDSSPSALQRAAWGISE 713

HERG-1 SSPGRRPRGDVESRLDALQRQLNRLETRLSADMATVLQLLQRQMTLVPPAYSAVTTPGPGPTSTSPLLPVS-PLPTL----TLDSLSQVS 1112
HERG-2 533
HERG-3 TESDL-TYGEVEQRLDLLQEQLNRLESQMTTDIQTILQLLQKQTTVVPPAYSMVTAGSEYQRPIIQLMRTSQPEASIKTDRSFSPSSQCP 802

HERG-1 QPM---------ACEEIPPG------------APELPQEG------------------STPRLSLPGQ-IGALTSQPLHRHGSDPG---S 1159
HERG-2 533
HERG-3 EPLDLEKSKLKSKESISSGVHLNTASEDNLTSLLKQDSDLSLELHLRQRKTYVHPIRHPSLPDSSLSTVGIVGLHRHVSDPGLPGK 888
```

Decoration 'Decoration #1': Box residues that match the Consensus exactly.

Fig. 2B

POLYNUCLEOTIDES ENCODING HERG-3

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention relates to the field of genes encoding ion channels, and the proteins encoded thereby, and more particularly to genes related to the human Erg gene.

A family of genes that encode potassium ion channel proteins have been identified in and isolated from, various organisms including *C. elegans,* Drosophila, mouse, rat, and humans. The members of the gene family are classified into subfamilies (eag, elk, and erg) on the basis of sequence similarity. The Eag family is named for the original isolate from Drosophila (ether-a go-go or eag). The Elk family includes genes that encode eag-like potassium ion channels. The Erg family includes eag-related genes.

Typically there is about 40–50% amino acid identity among proteins in the different subfamilies. Within a subfamily, the amino acid identity is about 60–70% even for proteins from different species. The human Erg ion-channel gene (Herg) corresponds to the LQT-2 genetic locus and maps to chromosome 7 q-35-36. Mutations in Herg can cause long-QT (LQT) syndrome, a relatively rare disorder that causes syncope and sudden death due to ventricular arrhythmia. The characteristic increased electrocardiographic Q-T interval evidences delayed repolarization of the cardiac action potential. At a molecular level, the delayed repolarization is linked with abnormal ion channel behavior. The Herg gene, in particular, is shown to be altered or defective in both acquired and inherited forms of LQT syndrome.

Herg ion channels are inwardly rectifying potassium channels. Herg channels have properties consistent with the gating properties of eag, and other, outwardly-rectifying, S4-containing potassium channels, but with the addition of an inactivation mechanism that attenuates potassium efflux during depolarization. It is thought that these properties of Herg channel function are critical to maintaining normal cardiac rhythmicity. The molecular mechanism by which Herg ion channels protect the heart against inappropriate rhythmicity is elucidated in Smith, P. L., et al., "The Inward Rectification Mechanism of the HERG Cardiac Potassium Channel," 379 *Nature* 33 (1996) and in Miller, C. "The Inconstancy of the Human Heart," 379 *Nature* 767 (1996).

The Herg gene that encodes the Herg potassium ion channel subunits was described by Warmke, J. W. and B. Ganetzky, "A Family of Potassium Channel Genes Related to eag in Drosophila and Mammals," 91 PNAS USA 3438–3442 (1994), incorporated herein by reference. The Herg DNA sequence is found at Genbank Accession Number U04270. A Drosophila erg gene was described by Titus, S. A., et al., "The Drosophila erg $K^+$ Channel Polypeptide Is Encoded by the Seizure Locus," 17 *J. Neuroscience* 875–881 (1997) and is reported at Genbank Accession Number U42204. A *C. elegans* erg gene is found at Accession Numbers U02425 and U02453 of the Genbank database. The two 10 kb pieces of genomic DNA therein disclosed encode amino acid sequences that align respectively to the N-and C-terminal halves of the Drosophila erg polypeptide.

Because of the critical role played by the Herg gene in a well known human disease, and its use in the development of pharmacological therapies, it is important to determine whether additional Herg-like genes exist in humans that could also play an important role in LQT syndrome or in other diseases characteristic of abnormal ion channel function. Herg channels are also an important target for the development of new pharmaceuticals.

BRIEF SUMMARY OF THE INVENTION

The present invention is summarized in that novel genes disclosed herein encode Herg-type potassium channel proteins. Because of this similarity to Herg, (85% amino acid identity in the protein core) some or all of these genes will likely play an important physiological role in humans. Consequently, the genes have utility for genetic screening and gene therapy applications. Additionally, the potassium ion channels encoded by the genes can be important targets for developing new pharmaceuticals and for testing the specificity of pharmaceuticals for which Herg is the intended target. The novel gene sequences can also be used to identify corresponding genes in other clinically relevant organisms, such as rats and mice for developing animal models and test systems to evaluate the physiological function of normal and abnormal ion channels. Such models can also be used to evaluate drug therapies. It is an object of the present invention to provide two novel human genes related to Herg.

Other objects, advantages, and features of the present invention will become apparent upon consideration of the following detailed description.

BRIEF DESCRIPTION OF THE SEVERAL VIEWS OF THE DRAWINGS

FIG. 1A depicts rat cDNA rERG 6.1 obtained by screening a rat brain cDNA library with an Herg probe. FIG. 1B shows an alignment of Herg with rERG 6.1 and with two dbESTs having similarity to rERG 6.1. FIG. 1C shows a strategy for determining the nucleotide sequence of clone 11.1 that encodes Herg-2.

FIG. 2 depicts a comparison of the amino acid sequences of Herg (SEQ ID NO:13), Herg-2 (SEQ ID NO:2) and Herg-3 (SEQ ID NO:4) coding sequences. Sequences enclosed in a box are identical in two or three of the compared sequences.

DETAILED DESCRIPTION OF THE INVENTION

Figure 1A:
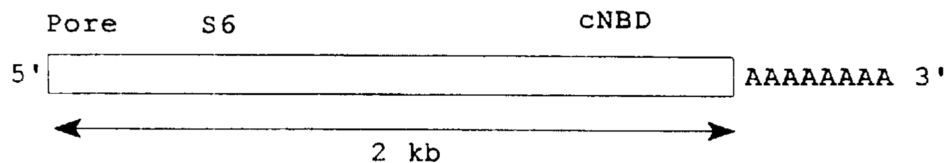
FIGS. 1A–C depicts a strategy for obtaining Herg-2 and for determining its nucleotide sequences.

A plurality of DNA sequences that encode Herg-type potassium ion channels are disclosed. A DNA sequence herein identified as Herg-2 is shown in SEQ ID NO:1. The amino acid sequence predicted from the Herg-2 cDNA sequence is shown in SEQ ID NO:2 A DNA sequence herein identified as Herg-3 is shown in SEQ ID NO:3. The amino acid sequence predicted from the Herg-3 cDNA sequence is shown in SEQ ID NO:4.

It is noted that the 5' end of the Herg-3 gene is not yet determined. Thus, the nucleotide and amino acid designations are intended to relate solely to the sequence listing presented, but not to the position of nucleotides and amino acids relative to the actual 5' or amino terminus of the Herg-3 gene or protein. Likewise, since an indeterminate number of internal amino acids are missing from both Herg-2, and an indeterminate number of N-terminal amino acids are missing from Herg-3, the reference to amino acid numbers and nucleotide numbers are merely exemplary and are intended to refer only to the nucleotides and amino acids designated herein, rather than to any particular position of the actual proteins or nucleic acids. Accordingly, any claim to a sequence that includes this portion of the gene is intended to encompass any sequence that includes the sequences upstream and downstream of the portion along with the sequences of that portion.

Several interesting aspects of the Herg-2 cDNA and protein are noted. The methionine codon shown as codon 15 of the Herg-2 protein may represent an alternate translation initiation sequence. Also, a section of the protein of approximately 100 amino acids (corresponding to about 300 base pairs of the cDNA sequence) is missing from the reported sequence. The missing bases are positioned just after the methionine-encoding ATG at nucleotide position 1567. The unknown bases are shown as N's in SEQ ID NO:1.

One of ordinary skill can distinguish the Herg-2 gene, and equivalent related genes, from the known Herg gene by virtue of DNA sequence differences. Herg-2 is distinguished from Herg and from Herg-3 in a segment toward the 5' end of the coding region, shown at bases 248–538 of SEQ ID NO: 1. This sequence is characteristic of Herg-2 and is not found in either the Herg or Herg-3 gene. These nucleic acid sequences are considered preferred embodiments of the invention. The Herg-2 cDNA sequence can also be described as a sequence that comprises bases 248–1567 (that is, the coding portion of the cDNA up to the missing internal portion of the gene), or as a sequence that comprises bases 248–2125 (the coding portion including the sequences upstream and downstream of the missing portion, as well as the missing portion itself). These sequences correspond to amino acids 1–97, 1–440, and 1–626 of the polypeptide encoded by the cDNA, respectively.

Likewise, the Herg-3 gene can also be distinguished from the Herg and Herg-2 genes by virtue of sequences located close to the 3' end of the cDNA and the corresponding polypeptide. Specifically, a sequence that characterizes the Herg-3 is shown between bases 2335 and 2616 of SEQ ID NO:3. This is considered a preferred embodiment of the invention. Other embodiments include a DNA molecule that includes a sequence of nucleotides as shown between bases 1561 and 2616 of SEQ ID NO:3, or a DNA molecule that includes a sequence of nucleotides as shown between bases 34 and 2616 of SEQ ID NO:3. Those nucleotides correspond to amino acids 768–861, 510–861 and 1–861 of the protein encoded by the Herg-3 cDNA (SEQ ID NO:4). Again, these sequences are not found in either Herg or Herg-2 and are considered to be characteristic of Herg-3.

It is noted that the invention is intended to cover all forms of the genes disclosed herein, including, for example, the genes in cDNA form or in genomic (unspliced) configuration.

Of course, one skilled in the art will appreciate that the characteristic sequences need not be identical at the DNA or the protein levels to those presented herein. Through the ordinary course of evolutionary mutation and somatic change in individuals, certain nucleotide and/or amino acid substitutions and small additions or deletions not affecting the activity of the proteins encoded thereby are to be expected. Specifically, it is also known that the degeneracy of the genetic code permits "wobble" at the third bases of codons. Thus, some nucleotide changes will have no bearing at all on the amino acids encoded by the genes. The applicants intend that the claims encompass all such modifications and variations of the sequences presented, without regard to the species of origin of the gene or protein or indeed whether isolated from a living organism or deliberately engineered in vitro using recombinant DNA methods available to the genetic engineer.

One skilled in the art will readily appreciate that, being in possession of sequences for Herg-2 and Herg-3, it is now possible to probe the genetic material of other animal species, including, but not limited to, mammals, rodents, nematodes, and the like.

Genetic probes targeted to the characteristic areas of the genes can be employed in much the same way that the Herg gene sequences were employed to obtain and isolate additional novel gene sequences.

Once in the possession of one of these novel genes, or an equivalent gene, one can insert the gene into an appropriate expression vector in order to obtain functional expression of the encoded channel polypeptides in a heterologous system. Such procedures are used to characterize the functional properties of the channels and to evaluate them as targets for pharmaceuticals. In addition, the channel polypeptides can be overproduced in a suitable host cell and then purified from the other cell proteins using methods available to those skilled in the art.

Among the known methods for expressing potassium channel genes, two ways are most often employed in the art: expression in a Xenopus oocyte system and expression in cultured mammalian cells. For the first method, a cDNA encoding the open reading frame of Herg-2 or Herg-3 or portions thereof can be incorporated into commercially available bacterial expression plasmids such as the pGEM (Promega) or pbluescript (Stratagene) vectors or one of their derivatives. After amplifying the expression plasmid in bacterial (*E. Coli*) cells the DNA is purified by standard methods. The incorporated potassium channel sequences in the plasmid DNA are then transcribed in vitro according to standard protocols. The RNA thus prepared is injected into Xenopus oocytes where it is translated and the resulting channel polypeptides are incorporated into the plasma membrane. The functional properties of these channels can then be investigated by electrophysiological, biochemical, pharmacological, and related methods. All the necessary procedures for functional expression of channels in Xenopus oocytes have been previously described in the literature and are well-known to one skilled in the art (Iverson, L. E., et al., "A-type potassium channels expressed from Shaker locus cDNA," *Proc. Natl. Acad. Sci. USA* 85:5723–5727 (1988); Timpe, L. C., et al., "Expression of functional potassium channels from Shaker cDNA in Xenopus oocytes," *Nature* 331:143–145 (1988); Root, M. J. and R. MacKinnon, "Identification of an external divalent cation-binding site in the pore of a cGMP-activated channel," *Neuron* 11:459–466 (1993), all of which are incorporated herein by reference in their entirety).

For the second method, a cDNA encoding the open reading frame of Herg-2 or Herg-3 or portions thereof can be incorporated into commercially available mammalian expression vectors such as the pcDNA series (Invitrogen) or equivalent vectors such as the GW1-CMV vector (British Biotech) or modifications thereof. The resulting constructs can then be transfected into any of several cultured mammalian cell lines such as HEK 293 cells, COS cells, etc. for stable or transient expression in the host cells. The transfected gene sequence is transcribed and translated by the host cells and the resulting channels are incorporated into the plasma membrane. The properties of these channels can then be investigated by electrophysiological techniques, binding studies, pharmacological assays, and similar methodologies. The protocols for obtaining expression of ion channels in mammalian cells is well-described in the literature and known to be those skilled in the art (Choi, K. L., et al., "Tetraethylammonium blockade distinguishes two inactivation mechanisms in voltage-activated $K^+$ channels," *Proc. Natl. Acad. Sci. USA* 88:5092–5095 (1991); Jurman M. E., et al., "Visual identification of individual transfected cells for electrophysiology using antibody coated beads," *Biotechniques* 17:876–881 (1994); Smith, P. L., et al., "The inward rectification mechanism of the HERG cardiac potassium channel," *Nature* 379:833–836 (1996); Stansfield, C. E., et al., "Elevation of intracellular calcium by muscarinic receptor activation induces a block of voltage-activated rat either a-go-go channels in a stably transfected cell line," *Proc. Natl. Acad. Sci. USA* 9910–9914 (1996), all of which are incorporated herein by reference in their entirety).

The following examples describe the isolation of Herg-2 and Herg-3. They are intended to be exemplary and not limiting on the scope of the invention. The same method may be used to isolate additional Herg-related genes.

By providing the characteristic cDNA and polypeptide sequences of additional members of the Herg subfamily, the inventors enable one to screen human and non-human animal subjects for the presence of normal and mutant forms of the Herg-2 and Herg-3 genes and polypeptide in human and non-human animals. Monoclonal or polyclonal antibodies directed against epitopes unique to Herg-2 or Herg-3 ion channels can now be produced using standard methods. Such antibodies could be used to monitor the role of potassium ion channels in normal or diseased subjects, although the shortcomings of antibody analysis have been noted above. To be useful, the antibodies would need to be non-cross-reactive with other proteins.

Herg-2 and Herg-3 appear to be active genes that are likely to encode an ion channel protein that can participate in disease processes of the type known to involve the Herg ion channels. It may be necessary to modulate the Herg-2 or Herg-3 ion channel activity to treat such a disease state, either by increasing or decreasing the activity. This can be accomplished by targeting pharmaceuticals to the protein encoded by Herg-2 or Herg-3. It will also be necessary to consider the physiological effect on those gene products on any treatment that modulates the activity of Herg ion channels.

In addition, it will also be possible to identify specific nucleotide or amino acid lesions that modulate Herg, Herg-2, or Herg-3 function. By modifying the Herg-2 or Herg-3 gene sequence, it will now be possible to develop genetic therapies for reversing the effects of such lesions, by replacing aberrant Herg-2 or Herg-3 genes with non-aberrant versions.

Moreover, even substitution of one amino acid for another, or additions or deletions of several amino acids may have little or no functional effect upon the protein encoded. The invention is intended to cover such variation as one skilled in the art would expect to find in such a gene or protein, whether such variation derives from natural variation among individuals or by deliberately introducing modification.

The invention will be more fully understood by considering the following examples, which are intended to be exemplary and not limiting on the scope of the invention.

EXAMPLES

A rat cDNA encoding a possible counterpart of Herg channels was obtained by screening a rat brain cDNA phage library (Stratagene Catalog Number 937502) with a partial Herg cDNA probe of approximately 2000 bases that spanned the segment from nucleotide 260–2300 of the Herg sequence published at Genbank Accession Number U04270. The library was inoculated onto eighteen large plates at a titer of 40,000 pfu/plate according to the manufacturer's instructions. The inoculated plates were then incubated at 37° C. for 14 hours. Phage were lifted from each plate onto nitrocellulose membranes. Phage DNA on the membranes was denatured and fixed to the membranes according to instructions from Stratagene.

The membranes containing the denatured and fixed DNA were incubated with the probe. The cDNA probe was $^{32}P$ labeled using a standard protocol for random primed DNA synthesis. After the radiolabelled Herg cDNA probe was denatured by boiling for 5 minutes, the probe ($5\times10^7$ total CPM) was incubated with the filters for 14 hours at 55° C. under the following hybridization conditions (2% mismatch): 2× SSCP(1× SSCP=120 mM sodium chloride, 15 mM sodium citrate, and 20 mM sodium phosphate), 1× Denhardtxs, 0.25 mg salmon sperm DNA, and 0.1% SDS. Hybridization was followed by two washes at 55° C. containing 0.5× SSC and 0.1% SDS.

A single positive hybridizing plaque (Rerg 6.1) was identified and was purified through secondary and tertiary rounds of phage growth and screening with the labeled probe, as above. The rat cDNA contained in this phage clone was purified and its length was determined by gel electrophoresis to be about 2.3 kb. Approximately 1 kb of the 5' end of the rat cDNA was sequenced using the Sequenase 2.0 dideoxy chain termination method (United States Biochemical) and an amino acid sequence was deduced from the cDNA sequence.

Figure 1B:
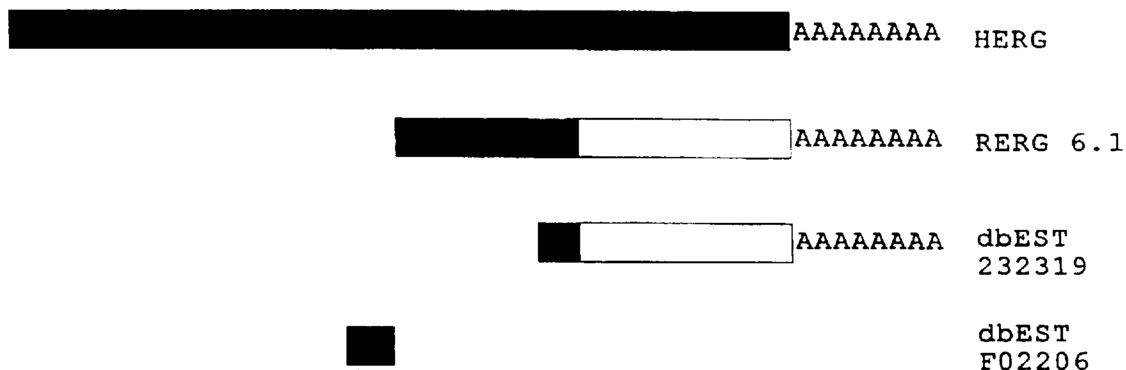

About 230 amino acids of the rat gene sequence aligned well with the Herg amino acid sequence in a region spanning the pore segment through the cyclic nucleotide binding domain (cNBD)-like segment of Herg. See FIGS. 1A and 1B. The region of alignment corresponds to amino acids 628 to 864 of Herg. No strong identity was found between the rat and human erg polypeptides beyond this region. However, the rat cDNA resembled the Herg sequence more closely than it did any other known polypeptide in the Eag family.

The rat erg sequence was compared against the dbEST database using the rat erg sequence as the query sequence. The sequence that showed the best match in this search was from a partial human cDNA having a Gen Bank Accession Number H96170. The EST revealed in the Genbank BLAST search was derived from I.M.A.G.E. Consortium (LLNL) Clone ID 232319 (Lawrence Livermore National laboratory, Livermore, Calif.). See Lennon, G. G., et al., "The I.M.A.G.E. Consortium: An Integrated Molecular Analysis of Genomes and Their Expression," 33 *Genomics,* 151–152 1996. The amino acid sequence that would be encoded by this partial human cDNA had greater similarity with Herg than it did with mammalian Eag or Elk polypeptides. Moreover, this putative polypeptide sequence aligned well with the rat erg sequence in the region beyond the cNBD-like segment where the rat sequence diverged from Herg.

rERG 6.1 also showed similarity to a dbEST cDNA clone having Genbank Accession Number F02206, which is unavailable for purchase.

The I.M.A.G.E. Consortium clone 232319 was purchased and was used to screen a human genomic library (Stratagene Catalog Number 945203) using the conditions used to screen the rat cDNA library. Eighteen filters, each containing genomic DNA from approximately 40,000 phage clones, were screened. Two phage clones gave positive hybridization signals in the primary screen and hybridized to the cDNA probe in secondary and tertiary screens.

Figure 1C:
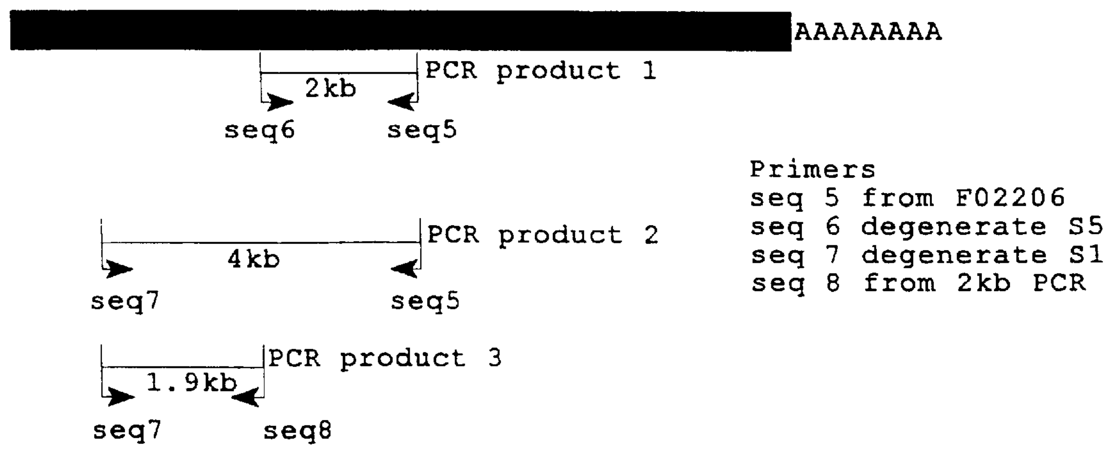

A strategy for obtaining Herg-2 and for determining its nucleotide sequence is shown in FIG. 1. One genomic clone (denoted 11.1) yielded a positive PCR-amplification product under the following conditions:

3' primer 5'-GGAATTCATGTCAATGCCATTGGTG-3' (SEQ ID NO: 5)

5' primer: 5'-TGGHTNGCNTGYATHTGGTA-3' (SEQ ID NO: 6)

Denaturation at 94° C. for one minute

Annealing at 40° C. for two minutes

Extension at 72° C. for four minutes, for a total of 2 rounds followed by 35 rounds of further amplification as above except with annealing at 48° C. for one minute. The 3' primer was based on bases 91–111 of the sequence of the dbEST clone having the Genbank accession number F02206. The degenerate 5' primer was based on the known SS sequences (Warmke et al., 1994) of Eag, Meag, Elk, and Herg.

The PCR amplification product (PCR Product Number 1) was about 1.8 kb, by gel electrophoresis. Since the expected size of the open reading frame in this region was about 450 base pairs by comparison with other known Eag family members, the size of the PCR product suggested that the genomic clone contained at least 1 intron. The PCR product was used as a template for DNA sequencing by the dye termination method using an automated sequencer from Applied Biosystems, Inc. The nucleotide sequence at either end of the PCR product was determined using the two PCR amplification primers as sequencing primers. The amplification product was determined to include 5' and 3' open reading frames flanking at least one intron having typical splice donor and splice acceptor sequences. The amino acid sequence of this region aligned well with the Herg sequence in a region spanning the segment from S5 to just beyond S6.

Additional sequence 5' to the S5 segment was obtained from genomic clone 11.1 by PCR amplification using a degenerate 5' primer based on the S1 segments of Eag, Meag, Elk and Herg (5'-TGGGACTGGNTNATHYT-3') (SEQ ID NO: 7). The 3' primer was the specific primer for the S6 segment previously specified (SEQ ID NO: 5). The resulting PCR-amplification product (PCR Product Number 2) was approximately 4 kb in size. This product was used as a template for yet another PCR reaction using the same 5' primer and a 3' primer based on the sequence obtained from the 5' end of PCR Product Number 1 (5'-CCTGCACCGAGGGGCCCGAGGCTGGG-3') (SEQ ID NO: 8). The PCR product of this third amplification (PCR Product Number 3) was about 2 kb in size and was sequenced as above. Again, the PCR amplification primers were used as sequencing primers. The 5' end of PCR Product Number 3 included a 260 base pair contiguous open reading frame preceding an intron splice donor site. A 230 base pair open reading frame was detected at the 3' end of PCR Product Number 3. The open reading frame sequences at the two ends of PCR Product Number 3 were connected (assuming a single 1500 base pair intron therebetween).

The 163 amino acid sequence encoded by the fragment aligned well with the Herg sequence in a region spanning the segment from S1 through S5.

DNA from genomic clone 11.1 was purified, digested with BamHI and separated by size. The five resulting bands total approximately 18 kb in length. The restriction fragments were transferred to a nylon filter by the Southern Blot procedure. The filter was then hybridized with a radioactive probe representing the 5' end of the Herg cDNA from nucleotide position 1 to 1444 of the published sequence. A single 1.2 kb restriction fragment showed positive hybridization. This band was subsequently isolated and subcloned into a pBlueScript vector. This cloned fragment was sequenced using vector-specific primers. The resulting sequence contained a complete open reading frame that extended from the S1 segment toward the amino terminus until an initiating methionine residue was reached.

I.M.A.G.E. Consortium CDNA Clone ID 232319 was also sequenced using vector-specific primers and several additional sequence-specific primers. A 252 base pair open reading frame at the 5' end of the clone precedes an untranslated segment of about 1 kb. The open reading frame encodes an amino acid sequence that spans the distal third of the cNBD-like segment through the carboxyl terminus. A composite amino acid sequence obtained from human genomic clone 11.1 and I.M.A.G.E. cDNA Clone ID 232319 represents a complete polypeptide sequence, with the exception of an inferred gap of about 100 amino acids between the end of S6 and the distal third of the cNBD-like The alignment of this olypeptide sequence with other members of the Erg subfamily as well as the position of introns in the Herg-2 genomic DNA clearly indicated that it represents not just an alternative splice variant of Herg, but rather a novel member of this subfamily in humans. Importantly, despite the close similarity with Herg, the two polypeptides are not identical. Therefore, the gene and polypeptide described here represents a second member of the erg subfamily in humans, dubbed Herg-2.

A third member of the erg subfamily in humans was obtained by screening a human brain cDNA library using two probes derived from the previously isolated Herg and Herg-2 cDNAs, as follows. The probes were obtained by PCR amplification. A 1515bp fragment spanning bases 1165 to 2680 of the Herg sequence was obtained by PCR amplification of Herg using 5' primer sequence 5'-ACCATCCTGCATTACAGC-3' (SEQ ID NO:9) and 3' primer sequence 5'-GGCTGCTCCGTGTCCTTG-3' (SEQ ID NO:10). A 630 bp fragment spanning bases 270 to 900 of the Herg-2 sequence was obtained by PCR amplification of Herg-2 using 3' primer sequence 5'-CCCTTGAAGTAGTGGACG-3' (SEQ ID NO:11) and 5' primer sequence 5'-GTGAGCATCAAACCTGGTGTCGCTATG-3' (SEQ ID NO:12). The amplified fragments were radioactively labeled as described previously.

A mixed probe containing both Herg and Herg-2 labeled fragments was used to screen a commercial human brain cDNA library (Clonetech catalogue number HL3002a). The library was plated and screened as described, supra, at a titer of 60,000 pfu/plate. Twenty-four plates were screened in total.

Positively hybridizing plaques were purified through secondary and tertiary rounds of phage growth and screening with the labeled probe as described. Approximately 500 base pairs of DNA sequence from each purified positively hybridizing phage clone were determined by the dye termination method using an automated sequencer from Applied Biosystems, Inc. Among 28 positively hybridizing clones thus analyzed, 6 encoded an amino acid sequence related to that of Herg and Herg-2 but clearly different from either previously identified member of this subfamily.

The complete 3 kilobase long nucleotide sequence of one clone, identified as 13B, containing a 3 kb insert, was determined. The open reading frame is complete from the first membrane-spanning region through the carboxy terminus. The sequence of the amino terminal end of the encoded polypeptide is still incomplete. A second overlapping cDNA, identified as clone 4D, should contain the missing sequence. On the basis of amino acid alignments with Herg and Herg-2 (see FIG. 2) the newly isolated cDNA clearly represents a third member of the Herg subfamily in humans, designated Herg-3. The present invention is not intended to be limited to the exemplified embodiment, but to encompass all such modifications and variations as come within the scope of the following claims.

We claim:

1. An isolated polynucleotide comprising nucleotides 2335 to 2616 as set forth in SEQ ID NO:3.

2. An isolated polynucleotide as claimed in claim 1 comprising nucleotides 1561 to 2616 as set forth in SEQ ID NO:3.

3. An isolated polynucleotide as claimed in claim 1 comprising nucleotides 34 to 2616 as set forth in SEQ ID NO:3.

4. A vector comprising the isolated polynucleotide of claim 1.

5. A vector as claimed in claim 4 comprising the isolated polynucleotide of claim 2.

6. A vector as claimed in claim 4 comprising the isolated polynucleotide of claim 3.

7. An isolated polynucleotide that encodes a polypeptide that comprises amino acids 768 to 861 as set forth in SEQ ID NO:4.

8. An isolated polynucleotide as claimed in claim 7 that encodes a polypeptide that comprises amino acids 510 to 861 as set forth in SEQ ID NO:4.

9. An isolated polynucleotide as claimed in claim 7 that encodes a polypeptide that comprises amino acids 1 to 861 as set forth in SEQ ID NO:4.

10. An isolated host cell transfected with a polynucleotide that encodes a polypeptide comprising amino acids 768 to 861 as set forth in SEQ ID NO:4.

11. An isolated host cell as claimed in claim 10 wherein the polynucleotide encodes a polypeptide comprising amino acids 510 to 861 as set forth in SEQ ID NO:4.

12. An isolated host cell as claimed in claim 10 wherein the polynucleotide encodes a polypeptide comprising amino acids 1 to 861 as set forth in SEQ ID NO:4.

* * * * *

UNITED STATES PATENT AND TRADEMARK OFFICE

CERTIFICATE OF CORRECTION

PATENT NO. : 5,986,081
DATED : Nov. 16, 1999
INVENTOR(S) : Barry S. Ganetzky, et al It is certified that error appears in the above-identified patent and that said Letters Patent is hereby corrected as shown below:

Column 1, after the title, insert the following:

--This invention was made with United States government support awarded by the following agencies:

NSF MCB-9408473; MCB-9014779
NIH 144-DN80; 144-ES89

The United States Government has certain rights in this invention.--

SEQUENCE LISTING

```
<160> NUMBER OF SEQ ID NOS: 13

<210> SEQ ID NO 1
<211> LENGTH: 3141
<212> TYPE: DNA
<213> ORGANISM: Homo sapien
<220> FEATURE:
<221> NAME/KEY: CDS
<222> LOCATION: (248)..(2128)
<220> FEATURE:
<221> NAME/KEY: unsure
<222> LOCATION: (1)
<223> OTHER INFORMATION: Unidentified at time of filing
<220> FEATURE:
<221> NAME/KEY: unsure
<222> LOCATION: (3)
<223> OTHER INFORMATION: Unidentified at time of filing
<220> FEATURE:
<221> NAME/KEY: unsure
<222> LOCATION: (12)
<223> OTHER INFORMATION: Unidentified at time of filing
<220> FEATURE:
<221> NAME/KEY: unsure
<222> LOCATION: (1568)..(1872)
<223> OTHER INFORMATION: Unidentified at time of filing
<220> FEATURE:
<221> NAME/KEY: unsure
<222> LOCATION: (3126)
<223> OTHER INFORMATION: Unidentified at time of filing
<220> FEATURE:
<221> NAME/KEY: unsure
<222> LOCATION: (3134)
<223> OTHER INFORMATION: Unidentified at time of filing

<400> SEQUENCE: 1

ntnattggcc gnttctccgc gcgagtggcg gccgctctag aactactgga tccccagggc      60

cctcataaag gaagacattc ttctaggggt gacctgttcc catcaggaac cctgaccata     120

gggagcctcc taagctcacc agagaggatc agcccatcag ctacccccttc tgtgggctct    180

tgtgtggaat gggtctatag atgtccatgg gcctggccct cccctgcctg gctccaccca     240

ctccagg atg ttt cca agg gag ctt gtg agc atc aaa cct ggt gtc gct      289
        Met Phe Pro Arg Glu Leu Val Ser Ile Lys Pro Gly Val Ala
         1               5                  10

atg ggg cgg agc cat acc cct cct ctt gca tcc caa ctc ctt ttc tct      337
Met Gly Arg Ser His Thr Pro Pro Leu Ala Ser Gln Leu Leu Phe Ser
 15                  20                  25                  30

gca ctt cct ctc gag gca tct gtc ccc tta gga act tgc ctt ctc aga      385
Ala Leu Pro Leu Glu Ala Ser Val Pro Leu Gly Thr Cys Leu Leu Arg
                 35                  40                  45

cgc ccc cca ccc cat ctc tcc ctc atc ccc tct gcc cac cag agc cgt      433
Arg Pro Pro Pro His Leu Ser Leu Ile Pro Ser Ala His Gln Ser Arg
             50                  55                  60

ggt cac cca ccc tct tcc cac tac acc ttc ccc agg cct cag ccc tct      481
Gly His Pro Pro Ser Ser His Tyr Thr Phe Pro Arg Pro Gln Pro Ser
         65                  70                  75

agg cca gtc tca cca gca ttg gct gcc ccg tgc ctg acc tcc ctc ggc      529
Arg Pro Val Ser Pro Ala Leu Ala Ala Pro Cys Leu Thr Ser Leu Gly
     80                  85                  90

ccc cac ccc cag gtc ctg tcc ctg ggc gcg gat gtg ctg ccg gag tac      577
```

-continued

```
Pro His Pro Gln Val Leu Ser Leu Gly Ala Asp Val Leu Pro Glu Tyr
 95                 100                 105                 110

aag ctg cag gcg ccg cgc atc cac cgc tgg acc atc ctg cac tac agc      625
Lys Leu Gln Ala Pro Arg Ile His Arg Trp Thr Ile Leu His Tyr Ser
                115                 120                 125

ccc ttc aag gcc gtg tgg gac tgg ctc atc ctg ctg ctg gtc atc tac      673
Pro Phe Lys Ala Val Trp Asp Trp Leu Ile Leu Leu Leu Val Ile Tyr
            130                 135                 140

acg gct gtc ttc acg ccc tac tca gcc gcc ttc ctg ctc agc gat cag      721
Thr Ala Val Phe Thr Pro Tyr Ser Ala Ala Phe Leu Leu Ser Asp Gln
        145                 150                 155

gac gaa tca cgg cgt ggg gcc tgc agc tat acc tgc agt ccc ctc act      769
Asp Glu Ser Arg Arg Gly Ala Cys Ser Tyr Thr Cys Ser Pro Leu Thr
    160                 165                 170

gtg gtg gat ctc atc gtg gac atc atg ttc gtc gtg gac atc gtc atc      817
Val Val Asp Leu Ile Val Asp Ile Met Phe Val Val Asp Ile Val Ile
175                 180                 185                 190

aac ttc cgc acc acc tat gtc aac acc aat gat gag gtg gtc agc cac      865
Asn Phe Arg Thr Thr Tyr Val Asn Thr Asn Asp Glu Val Val Ser His
                195                 200                 205

ccc cgc cgc atc gcc gtc cac tac ttc aag ggc tgg ttc ctc att gac      913
Pro Arg Arg Ile Ala Val His Tyr Phe Lys Gly Trp Phe Leu Ile Asp
            210                 215                 220

atg gtg gcc gcc atc cct ttc gac ctc ctg atc ttc cgc act ggc tcc      961
Met Val Ala Ala Ile Pro Phe Asp Leu Leu Ile Phe Arg Thr Gly Ser
        225                 230                 235

gat gaa acc aca acc ctg att ggg cta ttg aag aca gcg cgg ctg ctg     1009
Asp Glu Thr Thr Thr Leu Ile Gly Leu Leu Lys Thr Ala Arg Leu Leu
    240                 245                 250

cgg ctg gtg cgc gta gca cgg aag ctg gac cgc tac tct gag tat ggg     1057
Arg Leu Val Arg Val Ala Arg Lys Leu Asp Arg Tyr Ser Glu Tyr Gly
255                 260                 265                 270

gcg gct gtg ctc ttc ttg ctc atg tgc acc ttc gcg ctc ata gcg cac     1105
Ala Ala Val Leu Phe Leu Leu Met Cys Thr Phe Ala Leu Ile Ala His
                275                 280                 285

tgg ctg gcc tgc atc tgg tac gcc atc ggc aat gtg gag cgg ccc tac     1153
Trp Leu Ala Cys Ile Trp Tyr Ala Ile Gly Asn Val Glu Arg Pro Tyr
            290                 295                 300

cta gaa cac aag atc ggg tgg ctg gac agc ctg gct gtg cag ctt ggc     1201
Leu Glu His Lys Ile Gly Trp Leu Asp Ser Leu Ala Val Gln Leu Gly
        305                 310                 315

aag cgc tac aac ggc agc gac cca gcc tcg ggc ccc tcg gtg cag gac     1249
Lys Arg Tyr Asn Gly Ser Asp Pro Ala Ser Gly Pro Ser Val Gln Asp
    320                 325                 330

aag tat gtc aca gcc ctc tac ttc acc ttc agc agc ctc acc agc gtg     1297
Lys Tyr Val Thr Ala Leu Tyr Phe Thr Phe Ser Ser Leu Thr Ser Val
335                 340                 345                 350

ggc ttc ggc aat gtc tcg ccc aac acc aac tcc gag aag gtc ttc tcc     1345
Gly Phe Gly Asn Val Ser Pro Asn Thr Asn Ser Glu Lys Val Phe Ser
                355                 360                 365

atc tgc gtc atg ctc atc ggc tcc ctg atg tac gcc agc atc ttc ggg     1393
Ile Cys Val Met Leu Ile Gly Ser Leu Met Tyr Ala Ser Ile Phe Gly
            370                 375                 380

aac gtg tcc gcg atc atc cag cgc ctg tac tcg gga act gcc agg tac     1441
Asn Val Ser Ala Ile Ile Gln Arg Leu Tyr Ser Gly Thr Ala Arg Tyr
        385                 390                 395

cac atg cag atg ctg cga gta aaa gag ttc att cgc ttt cac caa atc     1489
His Met Gln Met Leu Arg Val Lys Glu Phe Ile Arg Phe His Gln Ile
    400                 405                 410

ccc aac cct ctg agg caa cgt ctt gaa gaa tat ttc cag cac gca tgg     1537
```

-continued

```
Pro Asn Pro Leu Arg Gln Arg Leu Glu Glu Tyr Phe Gln His Ala Trp
415                 420                 425                 430

act tac acc aat ggc att gac atg aac atg nnn nnn nnn nnn nnn nnn     1585
Thr Tyr Thr Asn Gly Ile Asp Met Asn Met Xaa Xaa Xaa Xaa Xaa Xaa
                435                 440                 445

nnn nnn nnn nnn nnn nnn nnn nnn nnn nnn nnn nnn nnn nnn nnn nnn     1633
Xaa Xaa Xaa Xaa Xaa Xaa Xaa Xaa Xaa Xaa Xaa Xaa Xaa Xaa Xaa Xaa
            450                 455                 460

nnn nnn nnn nnn nnn nnn nnn nnn nnn nnn nnn nnn nnn nnn nnn nnn     1681
Xaa Xaa Xaa Xaa Xaa Xaa Xaa Xaa Xaa Xaa Xaa Xaa Xaa Xaa Xaa Xaa
        465                 470                 475

nnn nnn nnn nnn nnn nnn nnn nnn nnn nnn nnn nnn nnn nnn nnn nnn     1729
Xaa Xaa Xaa Xaa Xaa Xaa Xaa Xaa Xaa Xaa Xaa Xaa Xaa Xaa Xaa Xaa
    480                 485                 490

nnn nnn nnn nnn nnn nnn nnn nnn nnn nnn nnn nnn nnn nnn nnn nnn     1777
Xaa Xaa Xaa Xaa Xaa Xaa Xaa Xaa Xaa Xaa Xaa Xaa Xaa Xaa Xaa Xaa
495                 500                 505                 510

nnn nnn nnn nnn nnn nnn nnn nnn nnn nnn nnn nnn nnn nnn nnn nnn     1825
Xaa Xaa Xaa Xaa Xaa Xaa Xaa Xaa Xaa Xaa Xaa Xaa Xaa Xaa Xaa Xaa
                515                 520                 525

nnn nnn nnn nnn nnn nnn nnn nnn nnn nnn nnn nnn nnn nnn nnn nnc     1873
Xaa Xaa Xaa Xaa Xaa Xaa Xaa Xaa Xaa Xaa Xaa Xaa Xaa Xaa Xaa Xaa
            530                 535                 540

acg agg ggc aag tcc agt gca gac gtg cgg gct ctg acc tac tgc gac     1921
Thr Arg Gly Lys Ser Ser Ala Asp Val Arg Ala Leu Thr Tyr Cys Asp
        545                 550                 555

ctg cac aag atc cag cgg gca gat ctg ctg gag gtg ctg gac atg tac     1969
Leu His Lys Ile Gln Arg Ala Asp Leu Leu Glu Val Leu Asp Met Tyr
    560                 565                 570

ccg gcc ttt gcg gag agc ttc tgg agt aag ctg gag gtc acc ttc aac     2017
Pro Ala Phe Ala Glu Ser Phe Trp Ser Lys Leu Glu Val Thr Phe Asn
575                 580                 585                 590

ctg cgg gac gca gcc ggg ggt ctc cac tca tcc ccc cga cag gct cct     2065
Leu Arg Asp Ala Ala Gly Gly Leu His Ser Ser Pro Arg Gln Ala Pro
                595                 600                 605

ggc agc caa gac cac caa ggt ttc ttt ctc agt gac aac agt cag atg     2113
Gly Ser Gln Asp His Gln Gly Phe Phe Leu Ser Asp Asn Ser Gln Met
            610                 615                 620

cag ccc ctc ccc tga gcatctcaga tgcatctggc ctctggcctg agctactgca     2168
Gln Pro Leu Pro
        625

ggaaatgccc ccaaggcaca gcccccaaag ccctcaggaa gacccagatt gctggcctct   2228

gaagctgggc tccaggctag agcagctcca ggcccagatg aacaggctgg agtcccgcgt   2288

gtcctcagac ctcagccgca tcttggagct cctccagaag cccatgcccc agggccacgc   2348

cagctacatt ctggaagccc ctgcctccaa tgacctggcc ttggttccta tagcctcgga   2408

gacgacgagt ccagggccca ggctgcccca gggctttctg cttcctgcac agaccccaag   2468

ctatggagac ttggatgact gtagtccaaa gcacaggaac tcctccccca ggatgcctca   2528

cctggctgtg gcaacggaca aaactctggc accatcctca gaacaggaac agcctgaggg   2588

gctctggcca cccctagcct cacctctaca tcccctggaa gtacaaggac tcatctgtgg   2648

tccctgcttc tcctccctcc ctgaacacct tggctctgtt cccaagcagc tggacttcca   2708

gagacatggc tcagatcctg gatttgcagg gaagttgggg ccactgaact ccaagataaa   2768

gacaccatga ggggactgaa ggtgggcaag gtgagagtta aggatcttgg ggaggtggcc   2828

gggtgcagtg gctcgcctgt aatcccagca ctttgggagg ccgaggcggg cggatcagac   2888

catcctggct aacacggtga aaccccacct ctactaaaat taaaaaagaa aaaaaatagc   2948
```

```
cgggcgtggt ggcaggcgcc tgtaatccca gctactgggg aggctgaggc aggagaatgg   3008

catgaacccg ggaggtggag gttgcaggga gccgaggccg caccactgca ctccagcctg   3068

ggtgacagag tgagactcca actcaaaaaa aaaaaaaaaa aaaacggcgg ccgccacntc   3128

gaaggnccaa aat                                                      3141
```

<210> SEQ ID NO 2
<211> LENGTH: 626
<212> TYPE: PRT
<213> ORGANISM: Homo sapien
<220> FEATURE:
<221> NAME/KEY: unsure
<222> LOCATION: (441)..(542)
<223> OTHER INFORMATION: Unidentified at time of filing

<400> SEQUENCE: 2

```
Met Phe Pro Arg Glu Leu Val Ser Ile Lys Pro Gly Val Ala Met Gly
  1               5                  10                  15

Arg Ser His Thr Pro Pro Leu Ala Ser Gln Leu Leu Phe Ser Ala Leu
             20                  25                  30

Pro Leu Glu Ala Ser Val Pro Leu Gly Thr Cys Leu Leu Arg Arg Pro
         35                  40                  45

Pro Pro His Leu Ser Leu Ile Pro Ser Ala His Gln Ser Arg Gly His
     50                  55                  60

Pro Pro Ser Ser His Tyr Thr Phe Pro Arg Pro Gln Pro Ser Arg Pro
 65                  70                  75                  80

Val Ser Pro Ala Leu Ala Ala Pro Cys Leu Thr Ser Leu Gly Pro His
                 85                  90                  95

Pro Gln Val Leu Ser Leu Gly Ala Asp Val Leu Pro Glu Tyr Lys Leu
            100                 105                 110

Gln Ala Pro Arg Ile His Arg Trp Thr Ile Leu His Tyr Ser Pro Phe
        115                 120                 125

Lys Ala Val Trp Asp Trp Leu Ile Leu Leu Leu Val Ile Tyr Thr Ala
    130                 135                 140

Val Phe Thr Pro Tyr Ser Ala Ala Phe Leu Leu Ser Asp Gln Asp Glu
145                 150                 155                 160

Ser Arg Arg Gly Ala Cys Ser Tyr Thr Cys Ser Pro Leu Thr Val Val
                165                 170                 175

Asp Leu Ile Val Asp Ile Met Phe Val Val Asp Ile Val Ile Asn Phe
            180                 185                 190

Arg Thr Thr Tyr Val Asn Thr Asn Asp Glu Val Val Ser His Pro Arg
        195                 200                 205

Arg Ile Ala Val His Tyr Phe Lys Gly Trp Phe Leu Ile Asp Met Val
    210                 215                 220

Ala Ala Ile Pro Phe Asp Leu Leu Ile Phe Arg Thr Gly Ser Asp Glu
225                 230                 235                 240

Thr Thr Thr Leu Ile Gly Leu Leu Lys Thr Ala Arg Leu Leu Arg Leu
                245                 250                 255

Val Arg Val Ala Arg Lys Leu Asp Arg Tyr Ser Glu Tyr Gly Ala Ala
            260                 265                 270

Val Leu Phe Leu Leu Met Cys Thr Phe Ala Leu Ile Ala His Trp Leu
        275                 280                 285

Ala Cys Ile Trp Tyr Ala Ile Gly Asn Val Glu Arg Pro Tyr Leu Glu
    290                 295                 300

His Lys Ile Gly Trp Leu Asp Ser Leu Ala Val Gln Leu Gly Lys Arg
305                 310                 315                 320
```

```
Tyr Asn Gly Ser Asp Pro Ala Ser Gly Pro Ser Val Gln Asp Lys Tyr
                325                 330                 335

Val Thr Ala Leu Tyr Phe Thr Phe Ser Ser Leu Thr Ser Val Gly Phe
            340                 345                 350

Gly Asn Val Ser Pro Asn Thr Asn Ser Glu Lys Val Phe Ser Ile Cys
        355                 360                 365

Val Met Leu Ile Gly Ser Leu Met Tyr Ala Ser Ile Phe Gly Asn Val
    370                 375                 380

Ser Ala Ile Ile Gln Arg Leu Tyr Ser Gly Thr Ala Arg Tyr His Met
385                 390                 395                 400

Gln Met Leu Arg Val Lys Glu Phe Ile Arg Phe His Gln Ile Pro Asn
                405                 410                 415

Pro Leu Arg Gln Arg Leu Glu Glu Tyr Phe Gln His Ala Trp Thr Tyr
            420                 425                 430

Thr Asn Gly Ile Asp Met Asn Met Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa Xaa Xaa Xaa
    450                 455                 460

Xaa Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa Xaa
                485                 490                 495

Xaa Xaa Xaa Xaa Xaa Xaa Xaa Xaa Xaa Xaa Xaa Xaa Xaa Xaa Xaa Xaa
            500                 505                 510

Xaa Xaa Xaa Xaa Xaa Xaa Xaa Xaa Xaa Xaa Xaa Xaa Xaa Xaa Xaa Xaa
        515                 520                 525

Xaa Xaa Xaa Xaa Xaa Xaa Xaa Xaa Xaa Xaa Xaa Xaa Xaa Xaa Thr Arg
    530                 535                 540

Gly Lys Ser Ser Ala Asp Val Arg Ala Leu Thr Tyr Cys Asp Leu His
545                 550                 555                 560

Lys Ile Gln Arg Ala Asp Leu Leu Glu Val Leu Asp Met Tyr Pro Ala
                565                 570                 575

Phe Ala Glu Ser Phe Trp Ser Lys Leu Glu Val Thr Phe Asn Leu Arg
            580                 585                 590

Asp Ala Ala Gly Gly Leu His Ser Ser Pro Arg Gln Ala Pro Gly Ser
        595                 600                 605

Gln Asp His Gln Gly Phe Phe Leu Ser Asp Asn Ser Gln Met Gln Pro
    610                 615                 620

Leu Pro
625
```

<210> SEQ ID NO 3
<211> LENGTH: 3142
<212> TYPE: DNA
<213> ORGANISM: Homo sapien
<220> FEATURE:
<221> NAME/KEY: CDS
<222> LOCATION: (34)..(2700)
<220> FEATURE:
<221> NAME/KEY: unsure
<222> LOCATION: (3)
<223> OTHER INFORMATION: Unidentified at time of filing
<220> FEATURE:
<221> NAME/KEY: unsure
<222> LOCATION: (17)
<223> OTHER INFORMATION: Unidentified at time of filing
<220> FEATURE:
<221> NAME/KEY: unsure
<222> LOCATION: (31)..(32)

<223> OTHER INFORMATION: Unidentified at time of filing
<220> FEATURE:
<221> NAME/KEY: unsure
<222> LOCATION: (432)
<223> OTHER INFORMATION: Unidentified at time of filing
<220> FEATURE:
<221> NAME/KEY: unsure
<222> LOCATION: (575)
<223> OTHER INFORMATION: Unidentified at time of filing
<220> FEATURE:
<221> NAME/KEY: unsure
<222> LOCATION: (1346)..(1348)
<223> OTHER INFORMATION: Unidentified at time of filing
<220> FEATURE:
<221> NAME/KEY: unsure
<222> LOCATION: (1733)
<223> OTHER INFORMATION: Unidentified at time of filing
<220> FEATURE:
<221> NAME/KEY: unsure
<222> LOCATION: (1735)
<223> OTHER INFORMATION: Unidentified at time of filing
<220> FEATURE:
<221> NAME/KEY: unsure
<222> LOCATION: (1737)
<223> OTHER INFORMATION: Unidentified at time of filing
<220> FEATURE:
<221> NAME/KEY: unsure
<222> LOCATION: (1744)
<223> OTHER INFORMATION: Unidentified at time of filing
<220> FEATURE:
<221> NAME/KEY: unsure
<222> LOCATION: (1746)
<223> OTHER INFORMATION: Unidentified at time of filing
<220> FEATURE:
<221> NAME/KEY: unsure
<222> LOCATION: (1758)
<223> OTHER INFORMATION: Unidentified at time of filing
<220> FEATURE:
<221> NAME/KEY: unsure
<222> LOCATION: (1773)
<223> OTHER INFORMATION: Unidentified at time of filing
<220> FEATURE:
<221> NAME/KEY: unsure
<222> LOCATION: (1798)
<223> OTHER INFORMATION: Unidentified at time of filing
<220> FEATURE:
<221> NAME/KEY: unsure
<222> LOCATION: (1812)
<223> OTHER INFORMATION: Unidentified at time of filing
<220> FEATURE:
<221> NAME/KEY: unsure
<222> LOCATION: (1830)..(1831)
<223> OTHER INFORMATION: Unidentified at time of filing
<220> FEATURE:
<221> NAME/KEY: unsure
<222> LOCATION: (1855)
<223> OTHER INFORMATION: Unidentified at time of filing
<220> FEATURE:
<221> NAME/KEY: unsure
<222> LOCATION: (1862)
<223> OTHER INFORMATION: Unidentified at time of filing
<220> FEATURE:
<221> NAME/KEY: unsure
<222> LOCATION: (1864)
<223> OTHER INFORMATION: Unidentified at time of filing
<220> FEATURE:
<221> NAME/KEY: unsure
<222> LOCATION: (1895)
<223> OTHER INFORMATION: Unidentified at time of filing
<220> FEATURE:
<221> NAME/KEY: unsure
<222> LOCATION: (1900)
<223> OTHER INFORMATION: Unidentified at time of filing
<220> FEATURE:
<221> NAME/KEY: unsure
<222> LOCATION: (1903)
<223> OTHER INFORMATION: Unidentified at time of filing
<220> FEATURE:
<221> NAME/KEY: unsure
<222> LOCATION: (1915)..(1916)

```
<223> OTHER INFORMATION: Unidentified at time of filing
<220> FEATURE:
<221> NAME/KEY: unsure
<222> LOCATION: (1920)
<223> OTHER INFORMATION: Unidentified at time of filing
<220> FEATURE:
<221> NAME/KEY: unsure
<222> LOCATION: (1934)
<223> OTHER INFORMATION: Unidentified at time of filing
<220> FEATURE:
<221> NAME/KEY: unsure
<222> LOCATION: (1943)
<223> OTHER INFORMATION: Unidentified at time of filing
<220> FEATURE:
<221> NAME/KEY: unsure
<222> LOCATION: (1971)
<223> OTHER INFORMATION: Unidentified at time of filing
<220> FEATURE:
<221> NAME/KEY: unsure
<222> LOCATION: (1990)
<223> OTHER INFORMATION: Unidentified at time of filing
<220> FEATURE:
<221> NAME/KEY: unsure
<222> LOCATION: (2001)
<223> OTHER INFORMATION: Unidentified at time of filing
<220> FEATURE:
<221> NAME/KEY: unsure
<222> LOCATION: (2013)..(2019)
<223> OTHER INFORMATION: Unidentified at time of filing
<220> FEATURE:
<221> NAME/KEY: unsure
<222> LOCATION: (3124)
<223> OTHER INFORMATION: Unidentified at time of filing
<220> FEATURE:
<221> NAME/KEY: unsure
<222> LOCATION: (3135)
<223> OTHER INFORMATION: Unidentified at time of filing
<220> FEATURE:
<221> NAME/KEY: unsure
<222> LOCATION: (3141)
<223> OTHER INFORMATION: Unidentified at time of filing

<400> SEQUENCE: 3

gancgattcg cttctcnttc ttcagataaa nnc att att gca ccc aag gtt aaa      54
                                     Ile Ile Ala Pro Lys Val Lys
                                       1               5

gat cga aca cac aat gtg act gag aaa gtg acc cag gtt ctc tct tta      102
Asp Arg Thr His Asn Val Thr Glu Lys Val Thr Gln Val Leu Ser Leu
         10                  15                  20

gga gca gat gtc cta cct gaa tac aaa ctg cag aca cca cgc atc aac      150
Gly Ala Asp Val Leu Pro Glu Tyr Lys Leu Gln Thr Pro Arg Ile Asn
     25                  30                  35

aag ttt acg ata ttg cac tac agc cct ttc aag gca gtc tgg gac tgg      198
Lys Phe Thr Ile Leu His Tyr Ser Pro Phe Lys Ala Val Trp Asp Trp
 40                  45                  50                  55

ctt atc ctg ctg ttg gtc ata tac act gct ata ttt act ccc tac tct      246
Leu Ile Leu Leu Leu Val Ile Tyr Thr Ala Ile Phe Thr Pro Tyr Ser
                 60                  65                  70

gca gcc ttc ctc ctc aat gac aga gaa gaa cag aag aga cga gaa tgt      294
Ala Ala Phe Leu Leu Asn Asp Arg Glu Glu Gln Lys Arg Arg Glu Cys
             75                  80                  85

ggc tat tct tgt agc cct ttg aat gtg gta gac ttg att gtg gat att      342
Gly Tyr Ser Cys Ser Pro Leu Asn Val Val Asp Leu Ile Val Asp Ile
         90                  95                 100

atg ttt atc ata gat att tta ata aac ttc aga aca aca tat gtt aat      390
Met Phe Ile Ile Asp Ile Leu Ile Asn Phe Arg Thr Thr Tyr Val Asn
    105                 110                 115

cag aat gaa gaa gtg gta agt gat ccc gcc aaa ata gca atn cac tac      438
Gln Asn Glu Glu Val Val Ser Asp Pro Ala Lys Ile Ala Xaa His Tyr
120                 125                 130                 135
```

```
ttc aaa ggc tgg ttc ctg att gac atg gtt gca gca att cct ttt gac      486
Phe Lys Gly Trp Phe Leu Ile Asp Met Val Ala Ala Ile Pro Phe Asp
            140                 145                 150

ttg ctg att ttt gga tca ggt tct gat gag aca aca aca tta att ggt      534
Leu Leu Ile Phe Gly Ser Gly Ser Asp Glu Thr Thr Thr Leu Ile Gly
            155                 160                 165

ctt ttg aag act gcc cga ctc ctc cgt ctt gtg cgc gtg gnc agg aaa      582
Leu Leu Lys Thr Ala Arg Leu Leu Arg Leu Val Arg Val Xaa Arg Lys
        170                 175                 180

ctg gat cga tat tca gaa tat ggc gct gct gtt cta atg ctc tca atg      630
Leu Asp Arg Tyr Ser Glu Tyr Gly Ala Ala Val Leu Met Leu Ser Met
    185                 190                 195

tgc atc ttt gcc ctg aat gca cac tgg ctg gct tgc att tgg tat gcg      678
Cys Ile Phe Ala Leu Asn Ala His Trp Leu Ala Cys Ile Trp Tyr Ala
200                 205                 210                 215

att ggg aat gta gaa agg cct tac ctg act gac aaa atc gga tgg ttg      726
Ile Gly Asn Val Glu Arg Pro Tyr Leu Thr Asp Lys Ile Gly Trp Leu
                220                 225                 230

gat tcc tta gga cag caa att ggg aaa cgt tac aat gac agt gac tca      774
Asp Ser Leu Gly Gln Gln Ile Gly Lys Arg Tyr Asn Asp Ser Asp Ser
            235                 240                 245

agt tct gga cca tcc att aaa gac aaa tac gtc aca gca ctt tat ttt      822
Ser Ser Gly Pro Ser Ile Lys Asp Lys Tyr Val Thr Ala Leu Tyr Phe
        250                 255                 260

acc ttc agc agt tta acc agt gta gga ttc ggg aat gtg tct cct aac      870
Thr Phe Ser Ser Leu Thr Ser Val Gly Phe Gly Asn Val Ser Pro Asn
    265                 270                 275

acg aat tcg gag aaa atc ttt tca att tgt gtc atg ttg att ggc tca      918
Thr Asn Ser Glu Lys Ile Phe Ser Ile Cys Val Met Leu Ile Gly Ser
280                 285                 290                 295

cta atg tat gca agc att ttt ggg aat gta tct gca att atc caa aga      966
Leu Met Tyr Ala Ser Ile Phe Gly Asn Val Ser Ala Ile Ile Gln Arg
                300                 305                 310

cta tac tcg gga act gcc agg tac cac atg cag atg ctg cga gta aaa     1014
Leu Tyr Ser Gly Thr Ala Arg Tyr His Met Gln Met Leu Arg Val Lys
            315                 320                 325

gag ttc att cgc ttt cac caa atc ccc aac cct ctg agg caa cgt ctt     1062
Glu Phe Ile Arg Phe His Gln Ile Pro Asn Pro Leu Arg Gln Arg Leu
        330                 335                 340

gaa gaa tat ttc cag cac gca tgg act tac acc aat ggc att gac atg     1110
Glu Glu Tyr Phe Gln His Ala Trp Thr Tyr Thr Asn Gly Ile Asp Met
    345                 350                 355

aac atg gtc cta aag ggt ttc cca gaa tgc tta caa gca gac att tgt     1158
Asn Met Val Leu Lys Gly Phe Pro Glu Cys Leu Gln Ala Asp Ile Cys
360                 365                 370                 375

cta cat ctc aac cag aca ttg ctg caa aac tgc aaa gcc ttt cgg ggg     1206
Leu His Leu Asn Gln Thr Leu Leu Gln Asn Cys Lys Ala Phe Arg Gly
                380                 385                 390

gca agt aaa ggt tgc ctt aga gct ttg gca atg aag ttc aaa acc acc     1254
Ala Ser Lys Gly Cys Leu Arg Ala Leu Ala Met Lys Phe Lys Thr Thr
            395                 400                 405

cat gca ctc caa gga gac acc ctc gtt cac tgt ggg gat gtc ctc act     1302
His Ala Leu Gln Gly Asp Thr Leu Val His Cys Gly Asp Val Leu Thr
        410                 415                 420

gca ctt tat ttc tta tcc aga ggc tcc att gaa atc tca aag ann nga     1350
Ala Leu Tyr Phe Leu Ser Arg Gly Ser Ile Glu Ile Ser Lys Xaa Xaa
    425                 430                 435

ctt gtg gtg gct att ctg gga aaa aat gat ata ttt gga gaa atg gtt     1398
Leu Val Val Ala Ile Leu Gly Lys Asn Asp Ile Phe Gly Glu Met Val
440                 445                 450                 455
```

-continued

```
cat ctt tat gcc aaa cct gga aag tct aat gca gat gta aga gcc ctc     1446
His Leu Tyr Ala Lys Pro Gly Lys Ser Asn Ala Asp Val Arg Ala Leu
                460                 465                 470

aca tac tgt gac ttg cat aag att cag cga gaa gac ttg tta gag gtt     1494
Thr Tyr Cys Asp Leu His Lys Ile Gln Arg Glu Asp Leu Leu Glu Val
            475                 480                 485

ttg gat atg tat cct gag ttt tct gat cac ttt cta aca aac cta gag     1542
Leu Asp Met Tyr Pro Glu Phe Ser Asp His Phe Leu Thr Asn Leu Glu
        490                 495                 500

ttg act ttc aac cta agg cat gag agc gca aag gct gat ctc cta cga     1590
Leu Thr Phe Asn Leu Arg His Glu Ser Ala Lys Ala Asp Leu Leu Arg
    505                 510                 515

tca caa tcc atg aat gat tca gaa gga gac aac tgt aaa cta aga aga     1638
Ser Gln Ser Met Asn Asp Ser Glu Gly Asp Asn Cys Lys Leu Arg Arg
520                 525                 530                 535

agg aaa ttg tca ttt gaa agt gaa gga gag aaa gaa aac agt acc aat     1686
Arg Lys Leu Ser Phe Glu Ser Glu Gly Glu Lys Glu Asn Ser Thr Asn
                540                 545                 550

gat cct gaa gac tct gca gat acc ata aga cat tat cag agt tcc cng     1734
Asp Pro Glu Asp Ser Ala Asp Thr Ile Arg His Tyr Gln Ser Ser Xaa
            555                 560                 565

ngn cct ttg nan aga aaa aaa gcn gat cct cct ctt tcn tct cct cca     1782
Xaa Pro Leu Xaa Arg Lys Lys Xaa Asp Pro Pro Leu Xaa Ser Pro Pro
        570                 575                 580

ttg atg atg aac aaa ncc ctc ttc tcc ggn ata gtt gac tct tct ccn     1830
Leu Met Met Asn Lys Xaa Leu Phe Ser Xaa Ile Val Asp Ser Ser Xaa
    585                 590                 595

ngg ata ggg gaa gcc tct ggg ctc nat ttt gna naa aca tgc ccc cct     1878
Xaa Ile Gly Glu Ala Ser Gly Leu Xaa Phe Xaa Xaa Thr Cys Pro Pro
600                 605                 610                 615

ccg gga gaa tgc cct tna tta nag nat cct ctt gcc nng atn tcc tgg     1926
Pro Gly Glu Cys Pro Xaa Leu Xaa Xaa Pro Leu Ala Xaa Xaa Ser Trp
                620                 625                 630

ctt cca anc ttg gga cna aaa aat tcc ctc ccc cgc ctg gag atn ccg     1974
Leu Pro Xaa Leu Gly Xaa Lys Asn Ser Leu Pro Arg Leu Glu Xaa Pro
            635                 640                 645

ttc ctc tgc cct tcc ncg aac tgc ctn ggg ttt ctc ttn nnn nnn gtg     2022
Phe Leu Cys Pro Ser Xaa Asn Cys Xaa Gly Phe Leu Xaa Xaa Xaa Val
        650                 655                 660

ccc acc tca gga aga atg cac ata gat aaa aga agt cac tct tgc aaa     2070
Pro Thr Ser Gly Arg Met His Ile Asp Lys Arg Ser His Ser Cys Lys
    665                 670                 675

gat atc act gac atg cga agc tgg gaa cga gaa aat gca cat ccc cag     2118
Asp Ile Thr Asp Met Arg Ser Trp Glu Arg Glu Asn Ala His Pro Gln
680                 685                 690                 695

cct gaa gac tcc agt cca tct gca ctt cag cga gct gcc tgg ggt atc     2166
Pro Glu Asp Ser Ser Pro Ser Ala Leu Gln Arg Ala Ala Trp Gly Ile
                700                 705                 710

tct gaa acc gaa agc gac ctc acc tac ggg gaa gtg gaa caa aga tta     2214
Ser Glu Thr Glu Ser Asp Leu Thr Tyr Gly Glu Val Glu Gln Arg Leu
            715                 720                 725

gat ctg ctc cag gag caa ctt aac agg ctt gaa tcc caa atg acc act     2262
Asp Leu Leu Gln Glu Gln Leu Asn Arg Leu Glu Ser Gln Met Thr Thr
        730                 735                 740

gac atc cag acc atc tta cag ttg ctg cag aaa caa acc act gtg gtc     2310
Asp Ile Gln Thr Ile Leu Gln Leu Leu Gln Lys Gln Thr Thr Val Val
    745                 750                 755

ccc cca gcc tac agt atg gta aca gca gga tca gaa tat cag aga ccc     2358
Pro Pro Ala Tyr Ser Met Val Thr Ala Gly Ser Glu Tyr Gln Arg Pro
760                 765                 770                 775
```

atc atc cag ctg atg aga acc agt caa ccg gaa gca tcc atc aaa act 2406
Ile Ile Gln Leu Met Arg Thr Ser Gln Pro Glu Ala Ser Ile Lys Thr
780 785 790 gac cga agt ttc agc cct tcc tca caa tgt cct gaa ttt cta gac ctt 2454
Asp Arg Ser Phe Ser Pro Ser Ser Gln Cys Pro Glu Phe Leu Asp Leu
795 800 805 gaa aaa tct aaa ctt aaa tcc aaa gaa tcc ctt tca agt ggg gtg cat 2502
Glu Lys Ser Lys Leu Lys Ser Lys Glu Ser Leu Ser Ser Gly Val His
810 815 820 ctg aac aca gct tca gaa gac aac ttg act tca ctt tta aaa caa gac 2550
Leu Asn Thr Ala Ser Glu Asp Asn Leu Thr Ser Leu Leu Lys Gln Asp
825 830 835 agt gat ctc tct tta gag ctt cac ctg cgg caa aga aaa act tac gtt 2598
Ser Asp Leu Ser Leu Glu Leu His Leu Arg Gln Arg Lys Thr Tyr Val
840 845 850 855 cat cca att agg cat cct tct ttg cca gat tca tcc cta agc act gta 2646
His Pro Ile Arg His Pro Ser Leu Pro Asp Ser Ser Leu Ser Thr Val
860 865 870 gga atc gtg ggt ctt cat agg cat gtt tct gat cct ggt ctt cca ggg 2694
Gly Ile Val Gly Leu His Arg His Val Ser Asp Pro Gly Leu Pro Gly
875 880 885 aaa taa tcattttgta ctatttactc cacatacaat gtaagtgctt ttaatggctg 2750
Lys ttttcctttt tctatttaaa tcctctctac ttgactcagg ggctcacaag gtaccattat 2810
atgcaaaagt actgtatatt ttcctaaatt gaagcttgta aggtaaaact gagcagttag 2870
gatgtaaata tacataagaa cttttggttc caaatgttaa aactgccagc atctcacggc 2930
accttatttt ttatttttat tttttaaatc acatgcatgt taggaaactc caatttctct 2990
tgcatggaga ctcctattta ctgcttttac taaaccagta cttcgttatg aaaatgcctt 3050
ccacgcaaat aagaaaccaa gggataaaac tgttcatgga tgcaactcaa attcagatga 3110
tcatcaaggc atgngaatcc atgtnccccc nc 3142

<210> SEQ ID NO 4
<211> LENGTH: 888
<212> TYPE: PRT
<213> ORGANISM: Homo sapien
<220> FEATURE:
<221> NAME/KEY: unsure
<222> LOCATION: (133)
<223> OTHER INFORMATION: Unidentified at time of filing
<220> FEATURE:
<221> NAME/KEY: unsure
<222> LOCATION: (181)
<223> OTHER INFORMATION: Unidentified at time of filing
<220> FEATURE:
<221> NAME/KEY: unsure
<222> LOCATION: (438)
<223> OTHER INFORMATION: Unidentified at time of filing
<220> FEATURE:
<221> NAME/KEY: unsure
<222> LOCATION: (439)
<223> OTHER INFORMATION: Unidentified at time of filing
<220> FEATURE:
<221> NAME/KEY: unsure
<222> LOCATION: (567)
<223> OTHER INFORMATION: Unidentified at time of filing
<220> FEATURE:
<221> NAME/KEY: unsure
<222> LOCATION: (568)
<223> OTHER INFORMATION: Unidentified at time of filing
<220> FEATURE:
<221> NAME/KEY: unsure
<222> LOCATION: (571)
<223> OTHER INFORMATION: Unidentified at time of filing
<220> FEATURE:
<221> NAME/KEY: unsure
<222> LOCATION: (575)
<223> OTHER INFORMATION: Unidentified at time of filing
<220> FEATURE:
<221> NAME/KEY: unsure
<222> LOCATION: (580)
<223> OTHER INFORMATION: Unidentified at time of filing
<220> FEATURE:
<221> NAME/KEY: unsure
<222> LOCATION: (589)
<223> OTHER INFORMATION: Unidentified at time of filing
<220> FEATURE:
<221> NAME/KEY: unsure
<222> LOCATION: (593)
<223> OTHER INFORMATION: Unidentified at time of filing
<220> FEATURE:
<221> NAME/KEY: unsure
<222> LOCATION: (599)
<223> OTHER INFORMATION: Unidentified at time of filing
<220> FEATURE:
<221> NAME/KEY: unsure
<222> LOCATION: (600)
<223> OTHER INFORMATION: Unidentified at time of filing
<220> FEATURE:
<221> NAME/KEY: unsure
<222> LOCATION: (608)
<223> OTHER INFORMATION: Unidentified at time of filing
<220> FEATURE:
<221> NAME/KEY: unsure
<222> LOCATION: (610)
<223> OTHER INFORMATION: Unidentified at time of filing
<220> FEATURE:
<221> NAME/KEY: unsure
<222> LOCATION: (611)
<223> OTHER INFORMATION: Unidentified at time of filing
<220> FEATURE:
<221> NAME/KEY: unsure
<222> LOCATION: (621)
<223> OTHER INFORMATION: Unidentified at time of filing
<220> FEATURE:
<221> NAME/KEY: unsure
<222> LOCATION: (624)
<223> OTHER INFORMATION: Unidentified at time of filing
<220> FEATURE:
<221> NAME/KEY: unsure
<222> LOCATION: (625)
<223> OTHER INFORMATION: Unidentified at time of filing
<220> FEATURE:
<221> NAME/KEY: unsure
<222> LOCATION: (628)
<223> OTHER INFORMATION: Unidentified at time of filing
<220> FEATURE:
<221> NAME/KEY: unsure
<222> LOCATION: (629)
<223> OTHER INFORMATION: Unidentified at time of filing
<220> FEATURE:
<221> NAME/KEY: unsure
<222> LOCATION: (634)
<223> OTHER INFORMATION: Unidentified at time of filing
<220> FEATURE:
<221> NAME/KEY: unsure
<222> LOCATION: (637)
<223> OTHER INFORMATION: Unidentified at time of filing
<220> FEATURE:
<221> NAME/KEY: unsure
<222> LOCATION: (646)
<223> OTHER INFORMATION: Unidentified at time of filing
<220> FEATURE:
<221> NAME/KEY: unsure
<222> LOCATION: (653)
<223> OTHER INFORMATION: Unidentified at time of filing
<220> FEATURE:
<221> NAME/KEY: unsure
<222> LOCATION: (656)
<223> OTHER INFORMATION: Unidentified at time of filing
<220> FEATURE:
<221> NAME/KEY: unsure
<222> LOCATION: (660)
<223> OTHER INFORMATION: Unidentified at time of filing
<220> FEATURE:
<221> NAME/KEY: unsure

```
<222> LOCATION: (661)
<223> OTHER INFORMATION: Unidentified at time of filing
<220> FEATURE:
<221> NAME/KEY: unsure
<222> LOCATION: (662)
<223> OTHER INFORMATION: Unidentified at time of filing

<400> SEQUENCE: 4

Ile Ile Ala Pro Lys Val Lys Asp Arg Thr His Asn Val Thr Glu Lys
  1               5                  10                  15

Val Thr Gln Val Leu Ser Leu Gly Ala Asp Val Leu Pro Glu Tyr Lys
             20                  25                  30

Leu Gln Thr Pro Arg Ile Asn Lys Phe Thr Ile Leu His Tyr Ser Pro
         35                  40                  45

Phe Lys Ala Val Trp Asp Trp Leu Ile Leu Leu Leu Val Ile Tyr Thr
     50                  55                  60

Ala Ile Phe Thr Pro Tyr Ser Ala Ala Phe Leu Leu Asn Asp Arg Glu
 65                  70                  75                  80

Glu Gln Lys Arg Arg Glu Cys Gly Tyr Ser Cys Ser Pro Leu Asn Val
                 85                  90                  95

Val Asp Leu Ile Val Asp Ile Met Phe Ile Ile Asp Ile Leu Ile Asn
            100                 105                 110

Phe Arg Thr Thr Tyr Val Asn Gln Asn Glu Glu Val Val Ser Asp Pro
        115                 120                 125

Ala Lys Ile Ala Xaa His Tyr Phe Lys Gly Trp Phe Leu Ile Asp Met
    130                 135                 140

Val Ala Ala Ile Pro Phe Asp Leu Leu Ile Phe Gly Ser Gly Ser Asp
145                 150                 155                 160

Glu Thr Thr Thr Leu Ile Gly Leu Leu Lys Thr Ala Arg Leu Leu Arg
                165                 170                 175

Leu Val Arg Val Xaa Arg Lys Leu Asp Arg Tyr Ser Glu Tyr Gly Ala
            180                 185                 190

Ala Val Leu Met Leu Ser Met Cys Ile Phe Ala Leu Asn Ala His Trp
        195                 200                 205

Leu Ala Cys Ile Trp Tyr Ala Ile Gly Asn Val Glu Arg Pro Tyr Leu
    210                 215                 220

Thr Asp Lys Ile Gly Trp Leu Asp Ser Leu Gly Gln Gln Ile Gly Lys
225                 230                 235                 240

Arg Tyr Asn Asp Ser Asp Ser Ser Ser Gly Pro Ser Ile Lys Asp Lys
                245                 250                 255

Tyr Val Thr Ala Leu Tyr Phe Thr Phe Ser Ser Leu Thr Ser Val Gly
            260                 265                 270

Phe Gly Asn Val Ser Pro Asn Thr Asn Ser Glu Lys Ile Phe Ser Ile
        275                 280                 285

Cys Val Met Leu Ile Gly Ser Leu Met Tyr Ala Ser Ile Phe Gly Asn
    290                 295                 300

Val Ser Ala Ile Ile Gln Arg Leu Tyr Ser Gly Thr Ala Arg Tyr His
305                 310                 315                 320

Met Gln Met Leu Arg Val Lys Glu Phe Ile Arg Phe His Gln Ile Pro
                325                 330                 335

Asn Pro Leu Arg Gln Arg Leu Glu Glu Tyr Phe Gln His Ala Trp Thr
            340                 345                 350

Tyr Thr Asn Gly Ile Asp Met Asn Met Val Leu Lys Gly Phe Pro Glu
        355                 360                 365

Cys Leu Gln Ala Asp Ile Cys Leu His Leu Asn Gln Thr Leu Leu Gln
    370                 375                 380
```

```
Asn Cys Lys Ala Phe Arg Gly Ala Ser Lys Gly Cys Leu Arg Ala Leu
385                 390                 395                 400

Ala Met Lys Phe Lys Thr Thr His Ala Leu Gln Gly Asp Thr Leu Val
                405                 410                 415

His Cys Gly Asp Val Leu Thr Ala Leu Tyr Phe Leu Ser Arg Gly Ser
            420                 425                 430

Ile Glu Ile Ser Lys Xaa Xaa Leu Val Val Ala Ile Leu Gly Lys Asn
        435                 440                 445

Asp Ile Phe Gly Glu Met Val His Leu Tyr Ala Lys Pro Gly Lys Ser
    450                 455                 460

Asn Ala Asp Val Arg Ala Leu Thr Tyr Cys Asp Leu His Lys Ile Gln
465                 470                 475                 480

Arg Glu Asp Leu Leu Glu Val Leu Asp Met Tyr Pro Glu Phe Ser Asp
                485                 490                 495

His Phe Leu Thr Asn Leu Glu Leu Thr Phe Asn Leu Arg His Glu Ser
            500                 505                 510

Ala Lys Ala Asp Leu Leu Arg Ser Gln Ser Met Asn Asp Ser Glu Gly
        515                 520                 525

Asp Asn Cys Lys Leu Arg Arg Arg Lys Leu Ser Phe Glu Ser Glu Gly
    530                 535                 540

Glu Lys Glu Asn Ser Thr Asn Asp Pro Glu Asp Ser Ala Asp Thr Ile
545                 550                 555                 560

Arg His Tyr Gln Ser Ser Xaa Xaa Pro Leu Xaa Arg Lys Lys Xaa Asp
                565                 570                 575

Pro Pro Leu Xaa Ser Pro Pro Leu Met Met Asn Lys Xaa Leu Phe Ser
            580                 585                 590

Xaa Ile Val Asp Ser Ser Xaa Xaa Ile Gly Glu Ala Ser Gly Leu Xaa
        595                 600                 605

Phe Xaa Xaa Thr Cys Pro Pro Pro Gly Glu Cys Pro Xaa Leu Xaa Xaa
    610                 615                 620

Pro Leu Ala Xaa Xaa Ser Trp Leu Pro Xaa Leu Gly Xaa Lys Asn Ser
625                 630                 635                 640

Leu Pro Arg Leu Glu Xaa Pro Phe Leu Cys Pro Ser Xaa Asn Cys Xaa
                645                 650                 655

Gly Phe Leu Xaa Xaa Xaa Val Pro Thr Ser Gly Arg Met His Ile Asp
            660                 665                 670

Lys Arg Ser His Ser Cys Lys Asp Ile Thr Asp Met Arg Ser Trp Glu
        675                 680                 685

Arg Glu Asn Ala His Pro Gln Pro Glu Asp Ser Ser Pro Ser Ala Leu
    690                 695                 700

Gln Arg Ala Ala Trp Gly Ile Ser Glu Thr Glu Ser Asp Leu Thr Tyr
705                 710                 715                 720

Gly Glu Val Glu Gln Arg Leu Asp Leu Leu Gln Glu Gln Leu Asn Arg
                725                 730                 735

Leu Glu Ser Gln Met Thr Thr Asp Ile Gln Thr Ile Leu Gln Leu Leu
            740                 745                 750

Gln Lys Gln Thr Thr Val Val Pro Pro Ala Tyr Ser Met Val Thr Ala
        755                 760                 765

Gly Ser Glu Tyr Gln Arg Pro Ile Ile Gln Leu Met Arg Thr Ser Gln
    770                 775                 780

Pro Glu Ala Ser Ile Lys Thr Asp Arg Ser Phe Ser Pro Ser Ser Gln
785                 790                 795                 800

Cys Pro Glu Phe Leu Asp Leu Glu Lys Ser Lys Leu Lys Ser Lys Glu
```

```
            805                 810                 815

Ser Leu Ser Ser Gly Val His Leu Asn Thr Ala Ser Glu Asp Asn Leu
            820                 825                 830

Thr Ser Leu Leu Lys Gln Asp Ser Asp Leu Ser Leu Glu Leu His Leu
        835                 840                 845

Arg Gln Arg Lys Thr Tyr Val His Pro Ile Arg His Pro Ser Leu Pro
    850                 855                 860

Asp Ser Ser Leu Ser Thr Val Gly Ile Val Gly Leu His Arg His Val
865                 870                 875                 880

Ser Asp Pro Gly Leu Pro Gly Lys
                885


<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5

ggaattcatg tcaatgccat tggtg                                           25


<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: allele
<222> LOCATION: (6)
<223> OTHER INFORMATION: degenerate oligonucleotide
<220> FEATURE:
<221> NAME/KEY: allele
<222> LOCATION: (9)
<223> OTHER INFORMATION: degenerate oligonucleotide

<400> SEQUENCE: 6

tgghtngcnt gyathtggta                                                 20


<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: allele
<222> LOCATION: (10)
<223> OTHER INFORMATION: degenerate oligonucleotide
<220> FEATURE:
<221> NAME/KEY: allele
<222> LOCATION: (12)
<223> OTHER INFORMATION: degenerate oligonucleotide

<400> SEQUENCE: 7

tgggactggn tnathyt                                                    17


<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence:
      oligonucleotide
```

<400> SEQUENCE: 8
cctgcaccga ggggcccgag gctggg 26

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: oligonucleotide

<400> SEQUENCE: 9
accatcctgc attacagc 18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: oligonucleotide

<400> SEQUENCE: 10
ggctgctccg tgtccttg 18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: oligonucleotide

<400> SEQUENCE: 11
cccttgaagt agtggacg 18

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: oligonucleotide

<400> SEQUENCE: 12
gtgagcatca aacctggtgt cgctatg 27

<210> SEQ ID NO 13
<211> LENGTH: 1159
<212> TYPE: PRT
<213> ORGANISM: Homo sapien

<400> SEQUENCE: 13

```
Met Pro Val Arg Arg Gly His Val Ala Pro Gln Asn Thr Phe Leu Asp
  1               5                  10                  15

Thr Ile Ile Arg Lys Phe Glu Gly Gln Ser Arg Lys Phe Ile Ile Ala
             20                  25                  30

Asn Ala Arg Val Glu Asn Cys Ala Val Ile Tyr Cys Asn Asp Gly Phe
         35                  40                  45

Cys Glu Leu Cys Gly Tyr Ser Arg Ala Glu Val Met Gln Arg Pro Cys
     50                  55                  60

Thr Cys Asp Phe Leu His Gly Pro Arg Thr Gln Arg Arg Ala Ala Ala
 65                  70                  75                  80
```

```
Gln Ile Ala Gln Ala Leu Leu Gly Ala Glu Glu Arg Lys Val Glu Ile
                 85                  90                  95

Ala Phe Tyr Arg Lys Asp Gly Ser Cys Phe Leu Cys Leu Val Asp Val
            100                 105                 110

Val Pro Val Lys Asn Glu Asp Gly Ala Val Ile Met Phe Ile Leu Asn
        115                 120                 125

Phe Glu Val Val Met Glu Lys Asp Met Val Gly Ser Pro Ala His Asp
    130                 135                 140

Thr Asn His Arg Gly Pro Pro Thr Ser Trp Leu Ala Pro Gly Arg Ala
145                 150                 155                 160

Lys Thr Phe Arg Leu Lys Leu Pro Ala Leu Leu Ala Leu Thr Ala Arg
                165                 170                 175

Glu Ser Ser Val Arg Ser Gly Gly Ala Gly Gly Ala Gly Ala Pro Gly
            180                 185                 190

Ala Val Val Val Asp Val Asp Leu Thr Pro Ala Ala Pro Ser Ser Glu
        195                 200                 205

Ser Leu Ala Leu Asp Glu Val Thr Ala Met Asp Asn His Val Ala Gly
    210                 215                 220

Leu Gly Pro Ala Glu Glu Arg Arg Ala Leu Val Gly Pro Gly Ser Pro
225                 230                 235                 240

Pro Arg Ser Ala Pro Gly Gln Leu Pro Ser Pro Arg Ala His Ser Leu
                245                 250                 255

Asn Pro Asp Ala Ser Gly Ser Ser Cys Ser Leu Ala Arg Thr Arg Ser
            260                 265                 270

Arg Glu Ser Cys Ala Ser Val Arg Arg Ala Ser Ser Ala Asp Asp Ile
        275                 280                 285

Glu Ala Met Arg Ala Gly Val Leu Pro Pro Pro Pro Arg His Ala Ser
    290                 295                 300

Thr Gly Ala Met His Pro Leu Arg Ser Gly Leu Leu Asn Ser Thr Ser
305                 310                 315                 320

Asp Ser Asp Leu Val Arg Tyr Arg Thr Ile Ser Lys Ile Pro Gln Ile
                325                 330                 335

Thr Leu Asn Phe Val Asp Leu Lys Gly Asp Pro Phe Leu Ala Ser Pro
            340                 345                 350

Thr Ser Asp Arg Glu Ile Ile Ala Pro Lys Ile Lys Glu Arg Thr His
        355                 360                 365

Asn Val Thr Glu Lys Val Thr Gln Val Leu Ser Leu Gly Ala Asp Val
    370                 375                 380

Leu Pro Glu Tyr Lys Leu Gln Ala Pro Arg Ile His Arg Trp Thr Ile
385                 390                 395                 400

Leu His Tyr Ser Pro Phe Lys Ala Val Trp Asp Trp Leu Ile Leu Leu
                405                 410                 415

Leu Val Ile Tyr Thr Ala Val Phe Thr Pro Tyr Ser Ala Ala Phe Leu
            420                 425                 430

Leu Lys Glu Thr Glu Glu Gly Pro Pro Ala Thr Glu Cys Gly Tyr Ala
        435                 440                 445

Cys Gln Pro Leu Ala Val Val Asp Leu Ile Val Asp Ile Met Phe Ile
    450                 455                 460

Val Asp Ile Leu Ile Asn Phe Arg Thr Thr Tyr Val Asn Ala Asn Glu
465                 470                 475                 480

Glu Val Val Ser His Pro Gly Arg Ile Ala Val His Tyr Phe Lys Gly
                485                 490                 495

Trp Phe Leu Ile Asp Met Val Ala Ala Ile Pro Phe Asp Leu Leu Ile
            500                 505                 510
```

```
Phe Gly Ser Gly Ser Glu Glu Leu Ile Gly Leu Leu Lys Thr Ala Arg
        515                 520                 525

Leu Leu Arg Leu Val Arg Val Ala Arg Lys Leu Asp Arg Tyr Ser Glu
    530                 535                 540

Tyr Gly Ala Ala Val Leu Phe Leu Leu Met Cys Thr Phe Ala Leu Ile
545                 550                 555                 560

Ala His Trp Leu Ala Cys Ile Trp Tyr Ala Ile Gly Asn Met Glu Gln
                565                 570                 575

Pro His Met Asp Ser Arg Ile Gly Trp Leu His Asn Leu Gly Asp Gln
            580                 585                 590

Ile Gly Lys Pro Tyr Asn Ser Ser Gly Leu Gly Gly Pro Ser Ile Lys
        595                 600                 605

Asp Lys Tyr Val Thr Ala Leu Tyr Phe Thr Phe Ser Ser Leu Thr Ser
    610                 615                 620

Val Gly Phe Gly Asn Val Ser Pro Asn Thr Asn Ser Glu Lys Ile Phe
625                 630                 635                 640

Ser Ile Cys Val Met Leu Ile Gly Ser Leu Met Tyr Ala Ser Ile Phe
                645                 650                 655

Gly Asn Val Ser Ala Ile Ile Gln Arg Leu Tyr Ser Gly Thr Ala Arg
            660                 665                 670

Tyr His Thr Gln Met Leu Arg Val Arg Glu Phe Ile Arg Phe His Gln
        675                 680                 685

Ile Pro Asn Pro Leu Arg Gln Arg Leu Glu Glu Tyr Phe Gln His Ala
    690                 695                 700

Trp Ser Tyr Thr Asn Gly Ile Asp Met Asn Ala Val Leu Lys Gly Phe
705                 710                 715                 720

Pro Glu Cys Leu Gln Ala Asp Ile Cys Leu His Leu Asn Arg Ser Leu
                725                 730                 735

Leu Gln His Cys Lys Pro Phe Arg Gly Ala Thr Lys Gly Cys Leu Arg
            740                 745                 750

Ala Leu Ala Met Lys Phe Lys Thr Thr His Ala Pro Pro Gly Asp Thr
        755                 760                 765

Leu Val His Ala Gly Asp Leu Leu Thr Ala Leu Tyr Phe Ile Ser Arg
    770                 775                 780

Gly Ser Ile Glu Ile Leu Arg Gly Asp Val Val Val Ala Ile Leu Gly
785                 790                 795                 800

Lys Asn Asp Ile Phe Gly Glu Pro Leu Asn Leu Tyr Ala Arg Pro Gly
                805                 810                 815

Lys Ser Asn Gly Asp Val Arg Ala Leu Thr Tyr Cys Asp Leu His Lys
            820                 825                 830

Ile His Arg Asp Asp Leu Leu Glu Val Leu Asp Met Tyr Pro Glu Phe
        835                 840                 845

Ser Asp His Phe Trp Ser Ser Leu Glu Ile Thr Phe Asn Leu Arg Asp
    850                 855                 860

Thr Asn Met Ile Pro Gly Ser Pro Gly Ser Thr Glu Leu Glu Gly Gly
865                 870                 875                 880

Phe Ser Arg Gln Arg Lys Arg Lys Leu Ser Phe Arg Arg Arg Thr Asp
                885                 890                 895

Lys Asp Thr Glu Gln Pro Gly Glu Val Ser Ala Leu Gly Pro Gly Arg
            900                 905                 910

Ala Gly Ala Gly Pro Ser Ser Arg Gly Arg Pro Gly Gly Pro Trp Gly
        915                 920                 925

Glu Ser Pro Ser Ser Gly Pro Ser Ser Pro Glu Ser Ser Glu Asp Glu
```

-continued

```
    930                 935                 940

Gly Pro Gly Arg Ser Ser Ser Pro Leu Arg Leu Val Pro Phe Ser Ser
945                 950                 955                 960

Pro Arg Pro Pro Gly Glu Pro Pro Gly Gly Glu Pro Leu Met Glu Asp
                965                 970                 975

Cys Glu Lys Ser Ser Asp Thr Cys Asn Pro Leu Ser Gly Ala Phe Ser
            980                 985                 990

Gly Val Ser Asn Ile Phe Ser Phe Trp Gly Asp Ser Arg Gly Arg Gln
        995                1000                1005

Tyr Gln Glu Leu Pro Arg Cys Pro Ala Pro Thr Pro Ser Leu Leu Asn
   1010                1015                1020

Ile Pro Leu Ser Ser Pro Gly Arg Arg Pro Arg Gly Asp Val Glu Ser
1025               1030                1035                1040

Arg Leu Asp Ala Leu Gln Arg Gln Leu Asn Arg Leu Glu Thr Arg Leu
               1045                1050                1055

Ser Ala Asp Met Ala Thr Val Leu Gln Leu Leu Gln Arg Gln Met Thr
           1060                1065                1070

Leu Val Pro Pro Ala Tyr Ser Ala Val Thr Thr Pro Gly Pro Gly Pro
       1075                1080                1085

Thr Ser Thr Ser Pro Leu Leu Pro Val Ser Pro Leu Pro Thr Leu Thr
   1090                1095                1100

Leu Asp Ser Leu Ser Gln Val Ser Gln Phe Met Ala Cys Glu Glu Leu
1105               1110                1115                1120

Pro Pro Gly Ala Pro Glu Leu Pro Gln Glu Gly Pro Thr Arg Arg Leu
               1125                1130                1135

Ser Leu Pro Gly Gln Leu Gly Ala Leu Thr Ser Gln Pro Leu His Arg
           1140                1145                1150

His Gly Ser Asp Pro Gly Ser
       1155
```